US007045636B2

(12) United States Patent
Palani et al.

(10) Patent No.: US 7,045,636 B2
(45) Date of Patent: May 16, 2006

(54) MCH ANTAGONISTS FOR THE TREATMENT OF OBESITY

(75) Inventors: Anandan Palani, Bridgewater, NJ (US); Sherry A. Shapiro, Belford, NJ (US); Mark D. McBriar, Stewartsville, NJ (US); Jing Su, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 227 days.

(21) Appl. No.: 10/278,468

(22) Filed: Oct. 23, 2002

(65) Prior Publication Data

US 2003/0144261 A1    Jul. 31, 2003

Related U.S. Application Data

(60) Provisional application No. 60/343,065, filed on Oct. 25, 2001.

(51) Int. Cl.
*C07D 207/00* (2006.01)
*C07D 213/00* (2006.01)
*A01N 43/40* (2006.01)
*A61K 31/435* (2006.01)

(52) U.S. Cl. ..................... 548/400; 546/1; 514/277; 514/359

(58) Field of Classification Search .............. 548/400; 546/1; 514/277, 359
See application file for complete search history.

(56) References Cited

U.S. PATENT DOCUMENTS 5,908,830 A    6/1999    Smith et al.
6,245,746 B1   6/2001    Chamberland et al.

FOREIGN PATENT DOCUMENTS

EP    1219294         3/2001
WO    WO 02/057233    7/2002
WO    WO 02/083134    10/2002

OTHER PUBLICATIONS

Shimada et al., Mice Lacking Melanin Concentrating Hormone are Hypophagic and Lean, *Nature*, vol. 396 (Dec. 17, 1998), pp. 670-673.
International Search Report PCT/US 02/33869 for CV01510K—6 Pages.

*Primary Examiner*—James O. Wilson
*Assistant Examiner*—Paul V. Ward
(74) *Attorney, Agent, or Firm*—William Y. Lee

(57) ABSTRACT

The present invention discloses compounds, which are novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

21 Claims, No Drawings

MCH ANTAGONISTS FOR THE TREATMENT OF OBESITY

CROSS REFERENCE TO RELATED APPLICATIONS

This application claims the benefit of U.S. Provisional Application No. 60/343,065 filed on Oct. 25, 2001.

FIELD OF THE INVENTION

This invention relates to antagonists of melanin-concentrating hormone (MCH) and their use in the treatment of obesity, eating disorders and diabetes, pharmaceutical compositions containing the compounds, and methods of treatment using the compounds.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670–673, MCH-deficient mice have reduced body weight and leanness due to hypophagia (reduced feeding). In view of their findings, it was suggested that antagonists of MCH action may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist.

U.S. Pat. No. 6,245,746, which issued, Jun. 12, 2001, discloses amide compounds which have efflux pump inhibitor activity related to the field of anti-microbial agents.

SUMMARY OF THE INVENTION

In one embodiment, this invention provides novel compounds having MCH antagonist activity. These compounds are represented by structural formula I:

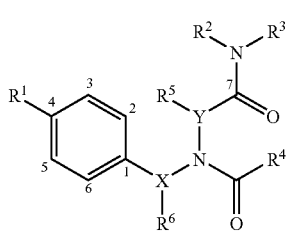

formula I or a pharmaceutically acceptable salt or solvate of said compound, wherein:

X is a single bond, —C—, —CH— or alkylene, and when X is a single bond, $R^6$ is absent and the carbon atom marked 1 is directly attached to N of N—Y;

Y is a single bond, —C—, —CH— or alkylene, and when Y is a single bond, $R^5$ is absent and the carbon atom marked 7 is directly attached to N of N—X;

$R^1$ is aryl or heteroaryl, wherein each of said aryl or heteroaryl can be unsubstituted or optionally independently substituted with one or more moieties which can be the same or different, each moiety being independently selected from the group consisting of CN, $CF_3$, halogen, alkyl, cycloalkyl, cycloalkylalkyl, haloalkyl, haloalkoxy, alkoxy and OH;

$R^2$ is H, alkyl, aryl or aralkyl wherein each of said aryl or aralkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH;

$R^3$ is H, alkyl, aryl or aralkyl wherein each of said aryl or aralkyl can be unsubstituted or optionally independently substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^4$ is selected from the group consisting of -alkylene-N$(R^7)_2$, —N(H)alkylene-N$(R^7)_2$, —O-alkylene-N$(R^7)_2$,

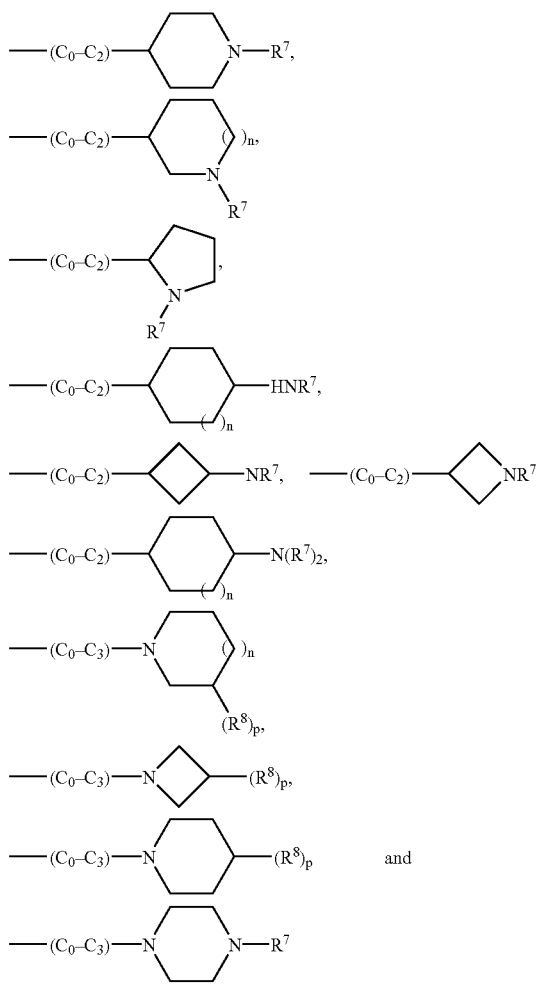

wherein each $R^7$ in said —N$(R^7)_2$, can be the same or different, each $R^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each $R^7$ can be joined together and with the nitrogen to which they are attached to form a 3 to 7-membered heterocyclyl ring;

p is 0 to 5 and when p is >1, the number of p moieties can be the same or different;

R⁵ is H or 1 or 2 substituents independently selected from alkyl or cycloalkyl;

R⁶ is H or 1 or 2 substituents independently selected from alkyl or cycloalkyl; and R⁸ is H, OH, alkoxy, alkyl, cycloalkyl, aryl, —N(H)R⁷, —N(H)C(O)alkyl, —N(H)C(O)aryl, —N(H)C(O)N(H)alkyl, —N(H)C(O)N(H)aryl, —N(H)S(O₂)alkyl or —N(H)S(O₂)aryl;

with the proviso that the carbons shown marked 1 and 6 on the aromatic ring, along with X—R⁶, can optionally form a 4 to 8 membered ring system.

A preferred group of compounds are those listed below in the Detailed Description as described in Formulae Ia, Ib and Ic.

The present invention also relates to compounds represented by structural formula II:

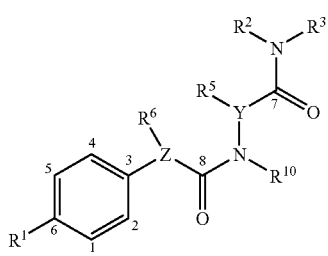

formula II or a pharmaceutically acceptable salt or solvate of said compound, wherein:

Y is a single bond, —C—, —CH— or alkylene, and when Y is a single bond, R⁵ is absent and the carbon atom marked 7 is directly attached to N of N—X;

Z is a single bond, —C—, —CH— or alkylene, and when Z is a single bond, R⁶ is absent and the carbon atom marked 1 is directly attached to the carbon atom marked 8;

R¹ is aryl or heteroaryl, wherein each of said aryl or heteroaryl can be unsubstituted or optionally independently substituted with one or more moieties which can be the same or different, each moiety being independently selected from the group consisting of CN, CF₃, halogen, alkyl, cycloalkyl, cycloalkylalkyl, haloalkyl, haloalkoxy, alkoxy and OH;

R² is H, alkyl, aryl or aralkyl wherein each of said aryl or aralkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH;

R³ is H, alkyl, aryl or aralkyl wherein each of said aryl or aralkyl can be unsubstituted or optionally independently substituted with one or more moieties which can be the same or different, each moiety being independently selected from the group consisting of CF₃, halogen, alkyl, cycloalkyl, cycloalkylalkyl, haloalkyl, haloalkoxy, alkoxy and OH;

R⁵ is H or 1 or 2 substituents independently selected from alkyl or cycloalkyl;

R⁶ is H or 1 or 2 substituents independently selected from alkyl or cycloalkyl;

R¹⁰ is selected from the group consisting -alkylene(R⁷)₂,

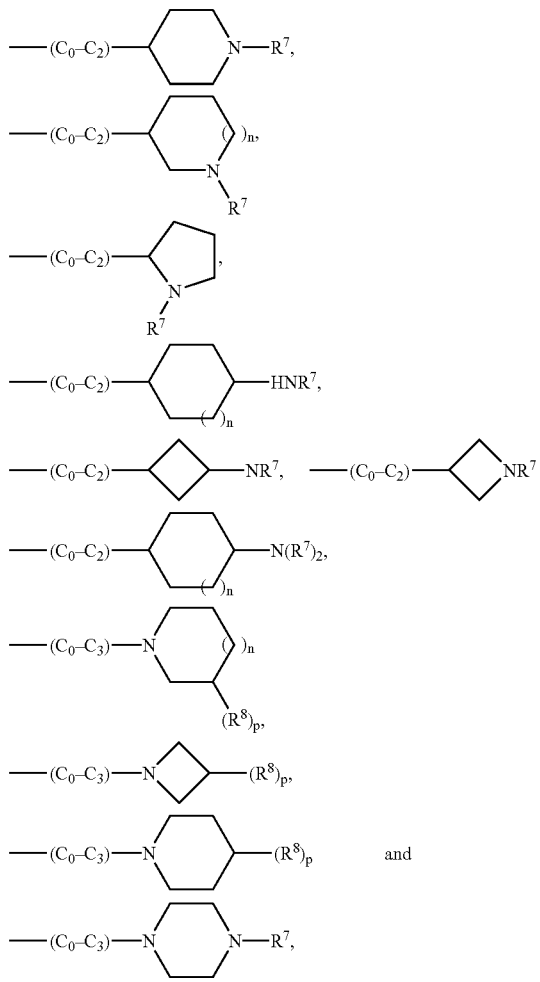

wherein each R⁷ in said —N(R⁷)₂, can be the same or different, each R⁷ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each R⁷ can be joined together and with the nitrogen to which they are attached to form a 3 to 7-membered heterocyclyl ring;

n is 0 or 1;

p is 0 to 5 and when p is >1, the number of p moieties can be the same or different; and R⁸ is H, OH, alkoxy, alkyl, cycloalkyl, aryl, —N(H)R⁷, —N(H)C(O)alkyl, —N(H)C(O)aryl, —N(H)C(O)N(H)alkyl, —N(H)C(O)N(H)aryl, —N(H)S(O₂)alkyl or —N(H)S(O₂)aryl;

with the proviso that the carbons shown marked 1 and 6 on the aromatic ring, along with X—R⁶, can optionally form a 4 to 8 membered ring system.

The compounds of formulae I and II, can be useful as MCH receptor antagonists and can be useful in the treatment of metabolic disorders such as obesity and eating disorders such as hyperphagia.

Another embodiment of this invention is directed to pharmaceutical compositions for the treatment of obesity which comprise an obesity treating amount of a compound of formula I or II, or a pharmaceutically acceptable salt of said compound, and a pharmaceutically acceptable carrier therefor.

DETAILED DESCRIPTION

In one embodiment, the present invention discloses MCH receptor antagonists represented by structural formulae I and II or a pharmaceutically acceptable salt or solvate thereof, wherein the various moieties are described above.

A preferred embodiment is a compound of formula Ia:

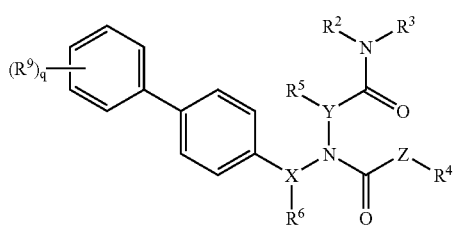

formula Ia or a pharmaceutically acceptable salt or solvate of said compound, wherein:

q is 0 to 5 and when q is >1, the number of q moieties can be the same or different;

X is —CH— or alkylene;

Y is a $CH_2$;

$R^2$ is H, alkyl, aryl or aralkyl wherein each of said aryl or aralkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH;

$R^3$ is H, alkyl, aryl or aralkyl wherein each of said aryl or aralkyl can be unsubstituted or optionally independently substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^4$ is -alkylene-$N(R^7)_2$, wherein the two $R^7$ moieties can be the same or different, each $R^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each $R^7$ can be joined together and with the nitrogen to which they are attached to form a 3 to 7-membered heterocyclyl ring, or $R^4$ is selected from

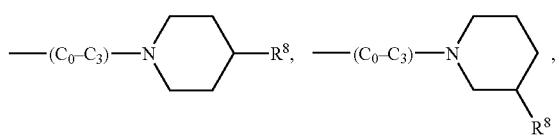

$R^5$ and $R^6$ can be the same or different, and are independently H or alkyl;

$R^8$ is H, OH, alkoxy, alkyl, cycloalkyl, aryl, —N(H)$R^7$, —N(H)C(O)alkyl, —N(H)C(O)N(H)alkyl or —N(H)S($O_2$)alkyl; and $R^9$ is alkyl, F, Cl, Br, I, $NO_2$, C(O)$NH_2$, C(O)N(H)R or N(H)C(O)R, wherein R is alkyl, $OCF_3$, $CF_3$ or CN.

Another preferred embodiment is a compound of formula Ib:

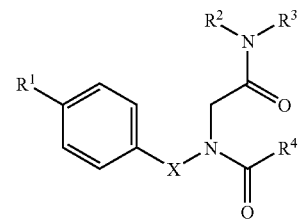

or a pharmaceutically acceptable salt or solvate of said compound, wherein:

X is an alkylene group;

$R^1$ is 3-cyanophenyl;

$R^2$ is H;

$R^3$ is a phenyl, wherein said phenyl is substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^4$ is -alkylene-$N(R^7)_2$, wherein the two $R^7$ moieties can be the same or different, each $R^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each $R^7$ can be joined together and with the nitrogen to which they are attached to form a 3 to 7-membered heterocyclyl ring; or $R^4$ is selected from

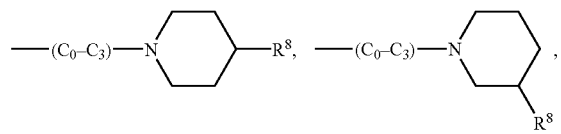

and $R^8$ is H, alkyl, cycloalkyl, aryl, —N(H)alkyl, —N(H)aryl, OH, alkoxy, —N(H)C(O)alkyl, —N(H)C(O)N(H)alkyl or —N(H)S($O_2$)alkyl.

Another preferred embodiment is a compound of formula Ic:

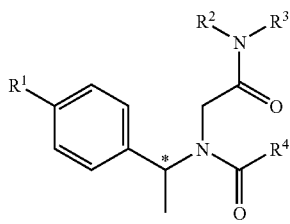

or a pharmaceutically acceptable salt or solvate of said compound, wherein:

$R^1$ is 3-cyanophenyl;

$R^2$ is H;

$R^3$ is a phenyl, wherein said phenyl is substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^4$ is -alkylene-$N(R^7)_2$, wherein the two $R^7$ moieties can be the same or different, each $R^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each $R^7$ can be joined together and with the nitrogen to which they are attached to form a 3 to 7-membered heterocyclyl ring; or $R^4$ is selected from

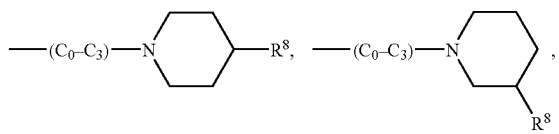

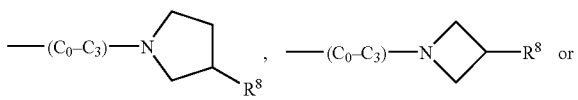

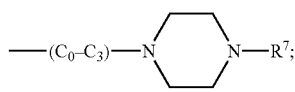

and $R^8$ is H, alkyl, cycloalkyl, aryl, —N(H)alkyl, —N(H)aryl, OH, alkoxy, —N(H)C(O)alkyl, —N(H)C(O)N(H)alkyl or —N(H)S($O_2$)alkyl.

A further preferred embodiment is a compound of formula IIa:

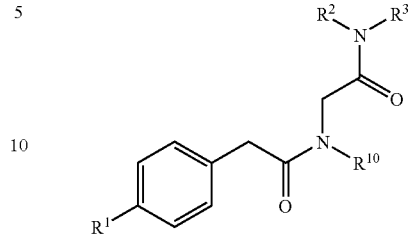

or a pharmaceutically acceptable salt or solvate of said compound, wherein:

$R^1$ is 3-cyanophenyl;

$R^2$ is H;

$R^3$ is a phenyl, wherein said phenyl is substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^8$ is H, OH, alkyl, cycloalkyl, aryl, —N(H)alkyl, —N(H)aryl, —N(H)C(O)alkyl, N(H)C(O)N(H)alkyl or —N(H)S($O_2$)alkyl; and;

$R^{10}$ is selected from the group consisting -alkylene($R^7)_2$,

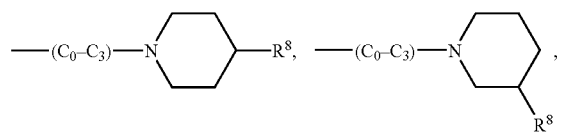

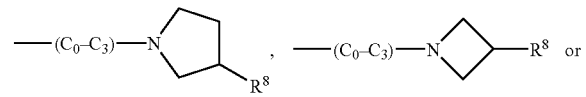

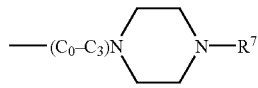

wherein the two $R^7$ moieties can be the same or different, each $R^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each $R^7$ can be joined together and with the nitrogen to which they are attached to form a 3 to 7-membered heterocyclyl ring.

A particularly preferred group of compounds are shown in Examples 1–65 and Tables 1, 2 and 3 of the Experimental Examples.

The present antagonists of formula I or II can be administered as racemic mixtures or enantiomerically pure compounds.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aryl" means an aromatic monocyclic or multicyclic ring system comprising about 6 to about 14 carbon atoms, preferably about 6 to about 10 carbon atoms. The aryl group can be optionally independently substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyll, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 3 to about 10 carbon atoms. Preferred cycloalkyl rings contain about 3 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkylalkyl group. Non-limiting examples of suitable cycloalkylalkyl groups include cyclopropylmethyl and cyclopropylethyl. The bond to the parent moiety is through the alkyl.

"Heterocyclylalkyl" means a heterocyclyl-alkyl group. Non-limiting examples of suitable heterocyclylalkyl groups include piperidinylmethyl and piperazinylmethyl. The bond to the parent moiety is through the alkyl.

"Halogen" means fluorine, chlorine, bromine, or iodine. Preferred are fluorine, chlorine or bromine, and more preferred are fluorine and chlorine.

"Halo" means fluoro, chloro, bromo, or iodo groups. Preferred are fluoro, chloro or bromo, and more preferred are fluoro and chloro.

"Ring system substituent" means a substituent attached to an aromatic or non-aromatic ring system, which, for example, replaces an available hydrogen on the ring system. Ring system substituents may be the same or different, each being independently selected from the group consisting of aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl; two adjacent ring system substituent groups can be joined together to form a methylenedioxy or ethyelenedioxy group.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, pyrrolidonyl, tetrahydrothiophenyl, and the like.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl.

Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in any of the formulae, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or II or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in antagonizing the dopamine receptor and thus producing the desired therapeutic, ameliorative or preventative effect.

The compounds of formulae I and II can form salts, which are also within the scope of this invention. Reference to the compounds of formulae I and II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when compounds of formulae I and II contain both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formulae I and II may be formed, for example, by reacting a compounds of formulae I and II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1 996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formulae I and II, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

N-oxides can form on a tertiary nitrogen present in an $X^1$, R or $R^2$ substituent, or on =N— in a heteroaryl ring substituent and are included in the compounds of formulae I and II.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I or II.

Compounds of formulae I and II can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I or II may form pharmaceutically acceptable salts with organic and inorganic acids. For example, pyrido-nitrogen atoms may form salts with strong acids, while tertiary amino groups may form salts with weaker acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Another aspect of this invention is a method of treating a patient (e.g., human) having a disease or condition mediated by MCH by administering a therapeutically effective amount of a compound of formula I or II, or a pharmaceutically acceptable salt of said compound to the patient.

A preferred dosage is about 0.001 to 100 mg/kg/day of the formula I or II compound. An especially preferred dosage is about 0.01 to 25 mg/kg/day of a compound of formula I or II, or a pharmaceutically acceptable salt of said compound.

Another aspect of this invention is directed to a method of treating obesity comprising administering to a patient in need of such treatment a therapeutically effective amount of a compound of formula I or II, or a pharmaceutically acceptable salt of said compound.

Another aspect of this invention is directed to a method for treating metabolic disorders such as obesity and eating disorders such as bulimia and anorexia comprising administering to a patient a therapeutically effective amount of a compound of formula I or II, or a pharmaceutically acceptable salt of said compound.

Another aspect of this invention is directed to a method for treating hyperlipidemia comprising administering to a patient a therapeutically effective amount of a compound of formula I or II, or a pharmaceutically acceptable salt of said compound.

Another aspect of this invention is directed to a method for treating cellulite and fat accumulation comprising administering to a patient a therapeutically effective amount of a compound of formula I or II, or a pharmaceutically acceptable salt of said compound.

Another aspect of this invention is directed to a method for treating type II diabetes comprising administering to a patient a therapeutically effective amount of a compound of formula I or II, or a pharmaceutically acceptable salt of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions which comprise an amount of a compound of formula I or II, or a pharmaceutically acceptable salt of said compound and a pharmaceutically acceptable carrier therefore.

This invention is also directed to pharmaceutical compositions for the treatment of obesity which comprise an obesity treating amount of a compound of formula I or II, or a pharmaceutically acceptable salt of said compound and a pharmaceutically acceptable carrier therefore.

Compounds of formulae I and II can be produced by processes known to those skilled in the art using either solution phase or solid phase synthesis as shown in the following reaction schemes, in the preparations and examples below.

Compounds of formulae Ia (where $R^6$ is H) and Ib are prepared according to the methods described in scheme 1.

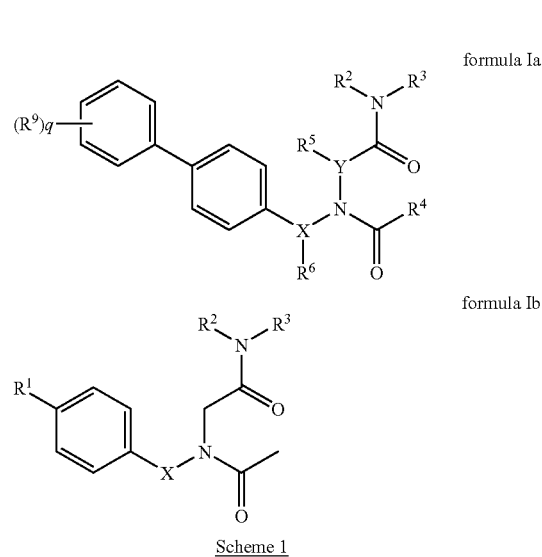

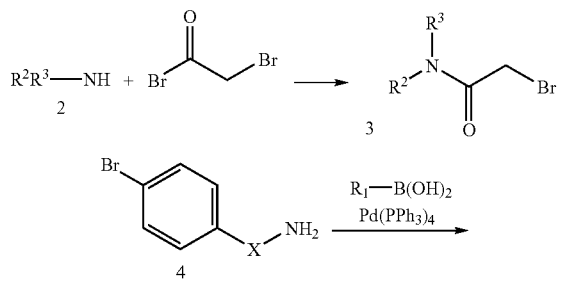

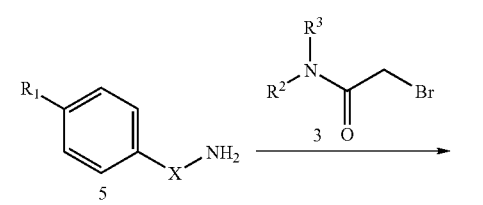

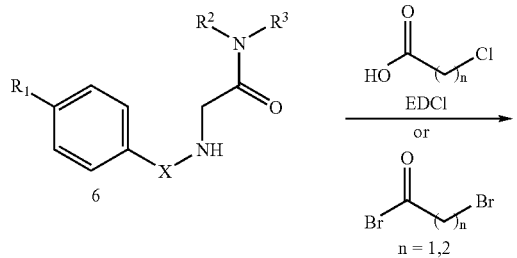

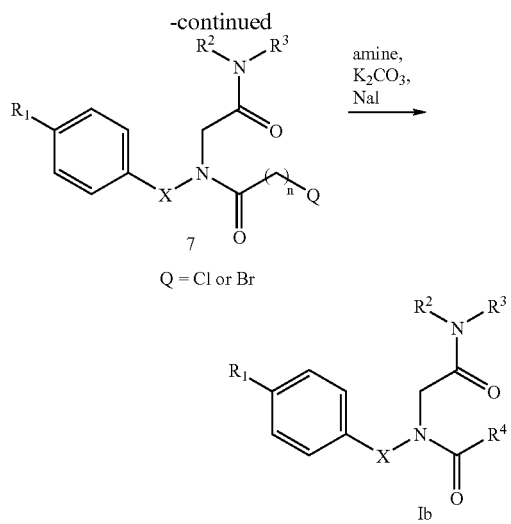

Aniline 2 is acylated with bromo acetylbromide to afford amide 3. Suzuki coupling of amine 4, in which X is a —(C1–C2)alkylene, with an aryl boronic acid gives biaryl amine 5. Nucleophilic displacement of bromide 3 with amine 5 affords the secondary amine 6, which is subsequently coupled to an acid in which n=1 or 2 under standard conditions to give chloride 7. Alternatively, amine 6 is acylated with bromoacetyl bromide to give bromide 7. Nucleophilic displacement of chloride or bromide 7 with the appropriate amine affords the desired di-amide Ib wherein $R^4$ is as descibed previously in the Detailed Descriptions. Alternatively, the sequence of steps can be changed so that the Suzuki coupling is carried out at the end of the sequence.

Compounds of formula Ia (where $R^6$ is alkyl) and Ic are prepared according to the methods described in Scheme 2.

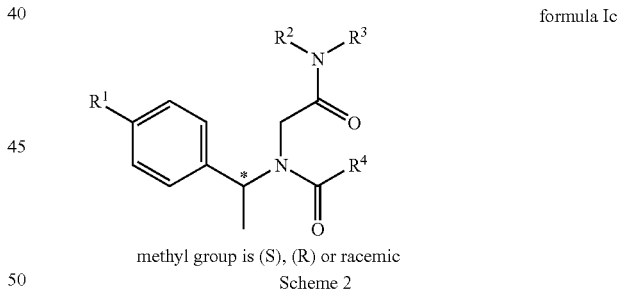

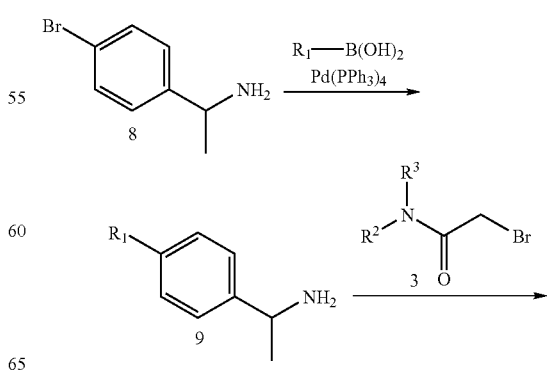

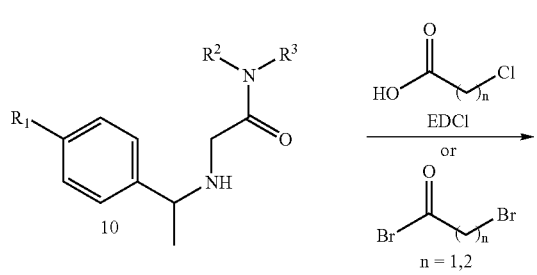

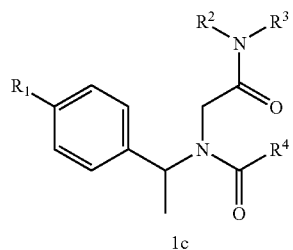

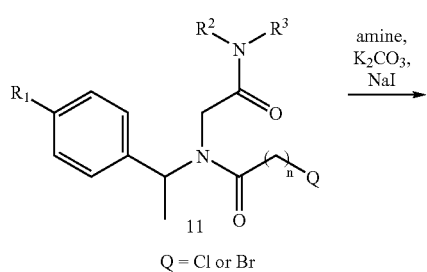

Suzuki coupling of 4-bromo-alpha-methylbenzyl amine 8 (chiral or racemic) with an aryl boronic acid gives biaryl amine 9. Nucleophilic displacement of bromide 3 with amine 9 affords the secondary amine 10, which is subsequently coupled to an acid in which n=1 or 2 under standard conditions to give chloride 11. Alternatively, amine 10 is acylated with bromoacetyl bromide to give bromide 11. Nucleophilic displacement of chloride or bromide 11 with the appropriate amine affords the desired di-amide Ic in which $R^4$ is as descibed previously in the Detailed Descriptions.

Alternatively, compounds of formulae Ib and Ic (where n=2) can be prepared according to Scheme 3.

Scheme 3

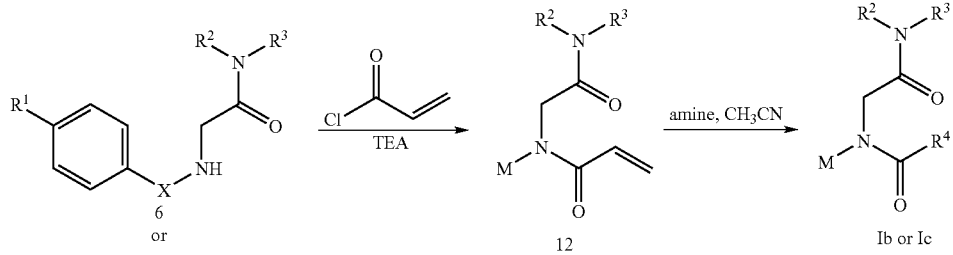

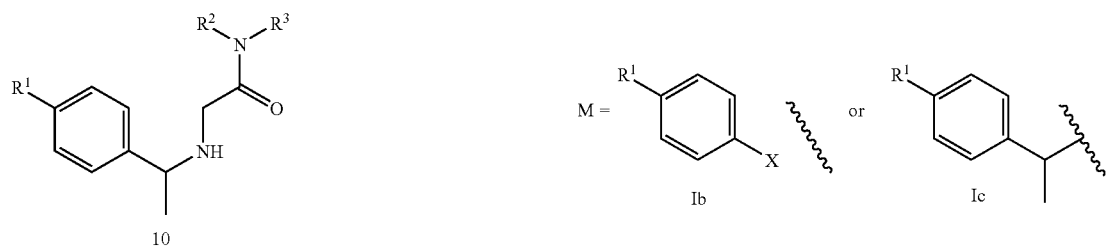

Amine 6 or 10 is acylated with acryloyl chloride in the presence of base such as TEA to give olefin 12. Addition of the appropriate amine affords the desired di-amide Ib or Ic in which $R^4$ is as described previously in the Detailed Descriptions.

Compounds of this invention of formula II are prepared according to the method shown below in Scheme 4.

Scheme 4

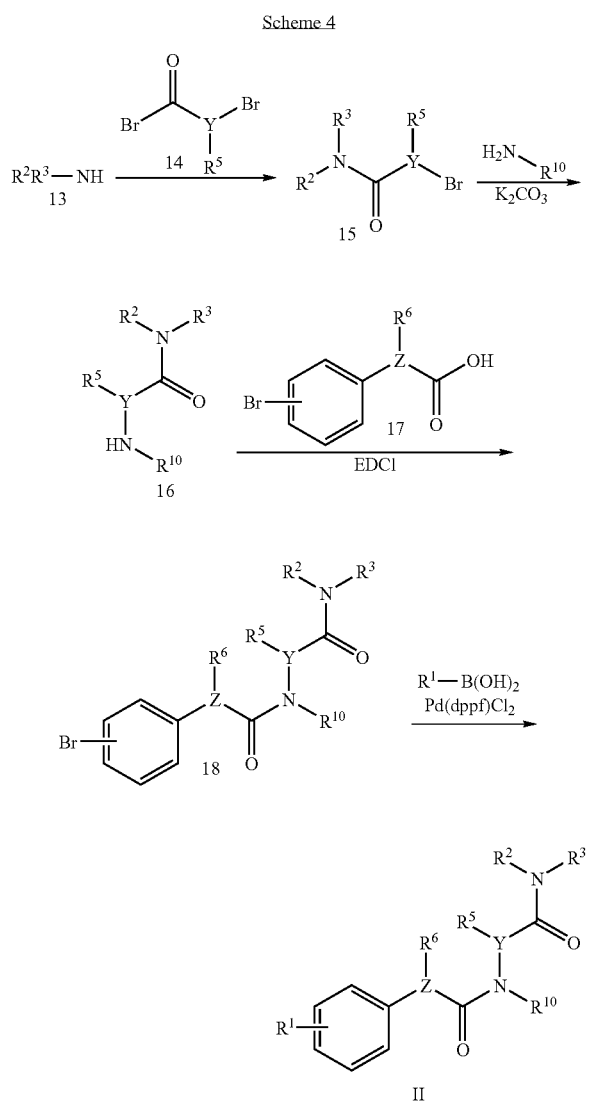

Amine 13 is acylated with an acid halide 14 to provide amide 15. Alkylation of 15 with an amine gives amine 16, which in turn can be coupled with acids 17 under standard conditions. Suzuki coupling of 18 with the appropriate boronic acid affords compounds of type II.

The following scheme illustrates the general method employed for synthesis of non-commercially available starting materials used in the above synthetic sequences (scheme 5). Amine A is acylated with an anhydride to provide amide B. Halogenation of B affords aryl halide C, which is subsequently deprotected with base to provide halogenated intermediates D.

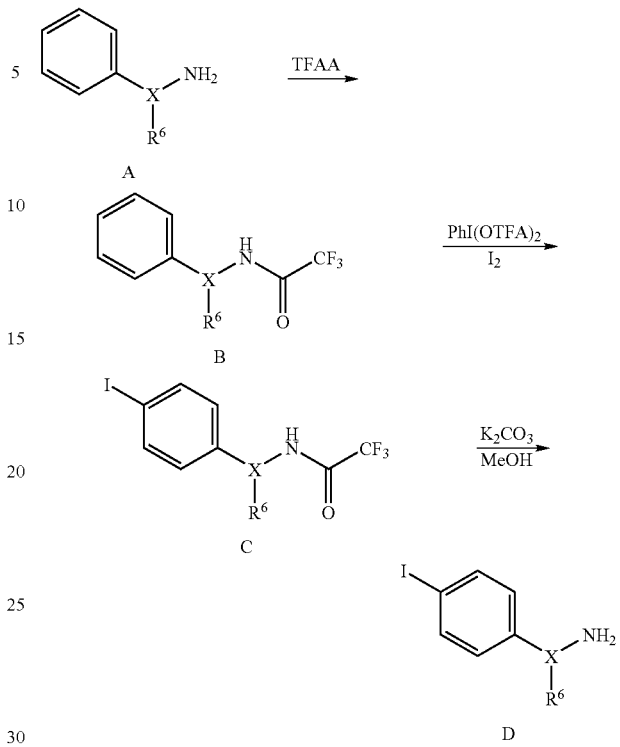

The compounds of formulae I and II exhibit MCH receptor antagonizing activity, which has been correlated with pharmaceutical activity for treating eating disorders, such as obesity and hyperphagia, and diabetes.

The compounds of formulae I and II display pharmacological activity in a test procedure designed to demonstrate MCH receptor antagonist activity. The compounds are non-toxic at pharmaceutically therapeutic doses.

Yet another aspect of this invention are combinations of a compound of formula I or II, or a pharmaceutically acceptable salt of said compound and one or more other compounds as illustrated below.

Accordingly, another aspect of this invention is a method for treating obesity comprising administering to a patient a. an amount of a first compound, said first compound being a formula I or II compound, or a pharmaceutically acceptable salt of said compound; and b. an amount of at least one more compound, said other compound (b) is selected from an antiobesity and/or anorectic agent such as a $\beta_3$ agonist, a thyromimetic agent, an anoretic agent, and an NPY antagonist wherein the amounts of the (a) and (b) compounds result in a therapeutic effect.

This invention is also directed to a pharmaceutical combination composition comprising: a therapeutically effective amount of a composition comprising a first compound, said first compound being a formula I or II compound, or a pharmaceutically acceptable salt of said compound; and at least one other compound selected from an antiobesity and/or anorectic agent such as a $\beta_3$ agonist, a thyromimetic agent, an anoretic, and an NPY antagonist; and/or optionally a pharmaceutical carrier, vehicle or diluent.

Another aspect of this invention is a kit comprising:

a. an amount of a formula I or II compound, or a pharmaceutically acceptable salt of said compound and a pharmaceutically acceptable carrier, vehicle or diluent in a first unit dosage form;

b. an amount of at least one antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a patient (e.g., a female or male human)

a. an amount of a first compound, said first compound being a formula I or II compound, or a pharmaceutically acceptable salt of said compound; and b. at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide wherein the amounts of the (a) and (b) compounds result in a therapeutic effect.

This invention is also directed to a pharmaceutical combination composition comprising: a therapeutically effective amount of a composition comprising a first compound, said first compound being a formula I or II compound, or a pharmaceutically acceptable salt of said compound;

at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide; and optionally a pharmaceutical carrier, vehicle or diluent.

Another aspect of this invention is a kit comprising:

a. an amount of a formula I or II compound, or a pharmaceutically acceptable salt of said compound and a pharmaceutically acceptable carrier, vehicle or diluent in a first unit dosage form;

b. at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide and a pharmaceutically acceptable carrier, vehicle or diluent in a second unit dosage form; and c. means for containing said first and second dosage forms wherein the amounts of the first and second compounds result in a therapeutic effect.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

This invention is also directed to pharmaceutical compositions for the treatment of metabolic disorders such as obesity, and eating disorders such as hyperphagia.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. The retention time and observed parent ion are given.

Compounds useful in this invention are exemplified by the following preparative examples, which should not be construed to limit the scope of the invention. Alternative mechanistic pathways and analogous structures within the scope of the invention would be apparent to those skilled in the art.

Starting materials are prepared by known methods and/or methods described in the Preparations.

The following solvents and reagents may be referred to by their abbreviations in parenthesis:

ethyl acetate (EtOAc);
methanol (MeOH);
triethylamine (TEA);
nuclear magnetic resonance spectroscopy (H NMR);
liquid chromatography mass spectrometry (LCMS);
high resolution mass spectrometry (HRMS);
milliliters (mL);
millimoles (mmol);
microliters (μl);
grams (g);
milligrams (mg);
room temperature (ambient) about 25° C. (rt);
1,2-dimethoxyethane (DME);
ethanol (EtOH);
N,N-dimethylformamide (DMF);
1-hydroxybenzotriazole (HOBt);
1-(3-dimethylaminopropyl)-3-ethyl carbodiimide hydrochloride (EDCl);
tert-butoxycarbonyl (Boc).

EXPERIMENTAL EXAMPLES

The following examples illustrate the preparation of some of the compounds of the invention and are not to be construed as limiting the invention disclosed herein.

Example 1

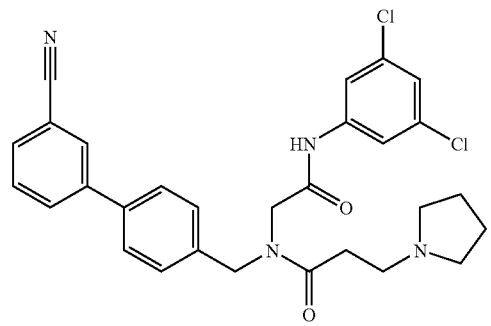

Step 1:

To a stirred solution of 3,5-dichloroaniline (10.4 g, 64.18 mmol) in methylene chloride, cooled to 0° C., was added bromoacetyl bromide (6.71 mL, 77.02 mmol) dropwise. The precipitous mixture stirred at 0° C. for 1 h. The reaction mixture was quenched with 10% NaOH and extracted with methylene chloride. The combined extracts were dried over $Na_2SO_4$ and concentrated to afford 16.21 g (90%) of bromide as a solid.

Step 2:

To a stirred solution of 4-bromobenzyl amine hydrochloride (12.2 g, 54.82 mmol) in 250 mL toluene:ethanol:$H_2O$ (3:1:1) was added 3-cyanophenyl boronic acid (16.11 g, 109.65 mmol), $Pd(PPh_3)_4$ (6.3 g, 5.48 mmol) and $Na_2CO_3$ (35 g, 330 mmol). The mixture was degassed with $N_2$, then heated to 100° C. for 24 h. The reaction mixture was concentrated then diluted with EtOAc, washed with $H_2O$, dried over $MgSO_4$, filtered, concentrated and chromatographed over silica gel (eluting with MeOH/$CH_2Cl_2$) to yield 7.44 g (65%) of biaryl amine as an oil.

Step 3:

To a stirred solution of amine formed in step 2, (3.88 g, 18.65 mmol) and bromide formed in step 1, (2.64 g, 9.32 mmol) in DMF (20 mL) was added $K_2CO_3$ (3.86 g, 27.98 mmol) and heated to 50° C. for 6 h. The reaction mixture was concentrated then diluted with EtOAc, washed with H₂O, dried over Na₂SO₄, concentrated and chromatographed over silica gel (eluting with EtOAc/hexanes) to yield 2.92 g (76%) of an amine.

Step 4:

To a stirred solution of amine formed in step 3, (0.41 g, 1.01 mmol) in methylene chloride (3 mL) was added 3-chloropropionic acid (0.22 g, 2.03 mmol) and EDCl (0.38 g, 2.03 mmol) and stirred at rt for 24 h. The reaction mixture was concentrated and used as a crude mixture for step 5.

Step 5:

To a stirred solution of chloride formed in step 4, (0.06 g, 0.12 mmol) in pyrrolidine (1 mL) was added K₂CO₃ (0.02 g, 0.12 mmol) and NaI (0.02 g, 0.12 mmol) and heated to 80° C. for 2.5 h. The reaction mixture was diluted with EtOAc, washed with NaHCO₃ solution, dried over MgSO₄, filtered and chromatographed (eluting with EtOH/EtOAc) to yield 0.03 g (51%) amine as a solid.

300 MHz—¹H NMR (CDCl₃)—9.08, *8.23 (s, 1H); 7.83 (s, 1H); 7.80–7.76 (m, 1H); 7.66–7.46 (m, 4H); 7.43–7.42 (d, 2H); 7.33–7.26 (d, 2H); 7.05 (s, 1H); 4.78, *4.73 (s, 2H); *4.16, 4.13 (s, 2H); 2.93–2.77 (m, 2H); 2.75–2.53 (m, 2H); 1.81–1.75 (m, 4H). Data provided is for a mixture of rotamers, * indicates the minor split peak. HRMS (M+H⁺) 535.1663 MCH Ki=21 nm Further, listed below is the experimental procedure for Example 9 in Table 1, which was also prepared according to Scheme 1.

Step 1:

To a stirred solution of 3,5-dichloroaniline (10.4 g, 64.18 mmol) in methylene chloride, cooled to 0° C., was added bromoacetyl bromide (6.71 mL, 77.02 mmol) dropwise. The precipitous mixture stirred at 0° C. for 1 h. The reaction mixture was quenched with 10% NaOH and extracted with methylene chloride. The combined extracts were dried over Na₂SO₄ and concentrated to afford 16.21 g (90%) of bromide as a solid.

Step 2:

To a stirred solution of 4-bromophenyl ethyl amine hydrochloride (12.6 g, 63.00 mmol) in 250 mL toluene:ethanol:H₂O (3:1:1) was added 3-cyanophenyl boronic acid, (13.71 g, 109.65 mmol), Pd(PPh₃)₄ (7.2 g, 6.3 mmol) and Na₂CO₃ (33 g, 330 mmol). The mixture was degassed with N₂, then heated to 100° C. for 24 h. The reaction mixture was concentrated then diluted with EtOAc, washed with H₂O, dried over MgSO₄, filtered, concentrated and chromatographed over silica gel (eluting with MeOH/CH₂Cl₂) to yield 8.2 g (58%) of biaryl amine as an oil.

Step 3:

To a stirred solution of amine formed in step 2, (2.0 g, 9.0 mmol) and bromide formed in step 1, (1.69 g, 6.00 mmol) in CH₃CN (30 mL) was added K₂CO₃ (1.65 g, 12.0 mmol) and heated to 50° C. for 6 h. The reaction mixture was concentrated then diluted with EtOAc, washed with H₂O, dried over Na₂SO₄, concentrated and chromatographed over silica gel (eluting with EtOAc/hexanes) to yield 1.6 g (64%) of an amine.

Step 4:

To a stirred solution of amine formed in step 3, (0.54 g, 1.27 mmol) in methylene chloride (10 mL) was added acryloyl chloride (0.114 g, 1.91 mmol) and triethyl amine (0.266 mL, 1.99 mmol) and stirred at rt for 24 h. The reaction mixture was diluted with methylene chloride, washed with water, dried over MgSO₄, filtered, concentrated and used in the next step with out purification.

Step 5:

To a stirred solution of olefin (0.030, 0.62 mmol) from step 4 in methylene chloride (1 mL) was added pyrrolidine (0.1 mL) and stirred at rt for 24 h. The reaction mixture was concentrated and purified to yield 0.02 g (59%) of an amine.

300 MHz—¹H NMR (CDCl₃)—9.28 (s, 1H); 7.83 (s, 1H); 7.80–7.76 (m, 1H); 7.66–7.46 (m, 4H); 7.43–7.42 (d, 2H); 7.33–7.26 (d, 2H); 7.05 (s, 1H); 4.42, *4.52 (s, 2H); *4.16, 4.13 (s, 2H); 3.73 (m, 2 H), 3.44–2.77 (m, 2H); 2.75–2.53 (m, 2H); 1.81–1.75 (m, 4H). Data provided is for a mixture of rotamers, * indicates the minor split peak. HRMS (M+H⁺) 549.1835

Examples 2–39

Employing preparative procedures similar to those described in Example 1 and Example 9, the following compounds were prepared:

TABLE 1

| Ex. | Structure | HRMS | MCH Ki (nm) |
|---|---|---|---|
| 2 | 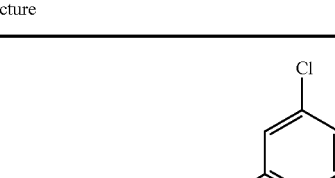 | 551.1612 | 3.7 |

TABLE 1-continued

| Ex. | Structure | HRMS | MCH Ki (nm) |
|---|---|---|---|
| 3 | 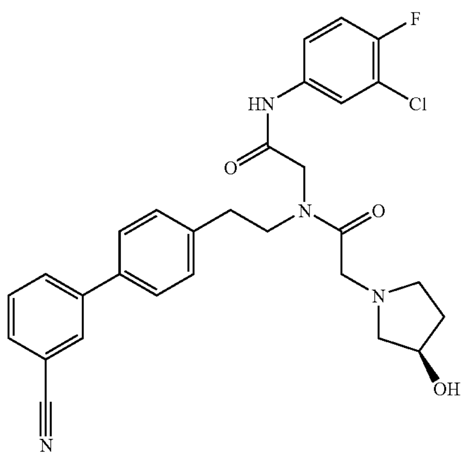 | 535.1919 | 3.7 |
| 4 | 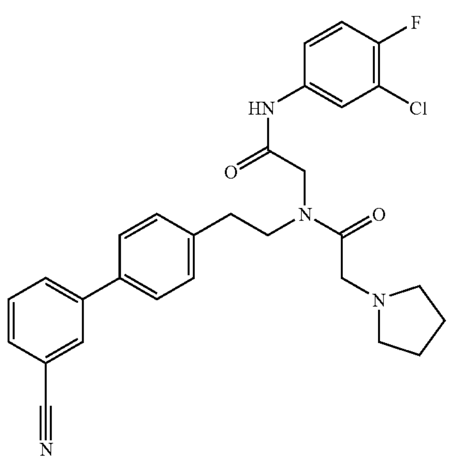 | 519.1957 | 5.3 |
| 5 | 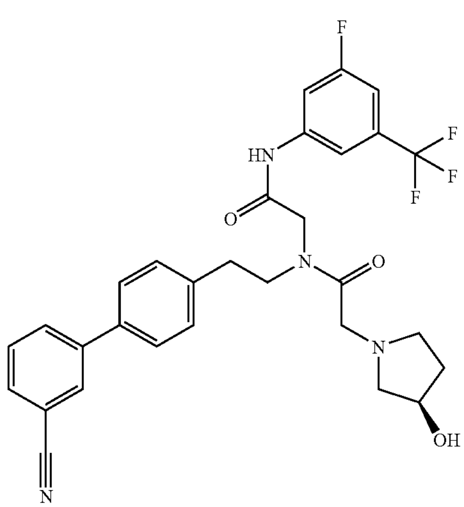 | 569.2174 | 6.7 |

TABLE 1-continued
| Ex. | Structure | HRMS | MCH Ki (nm) |
|---|---|---|---|
| 6 | 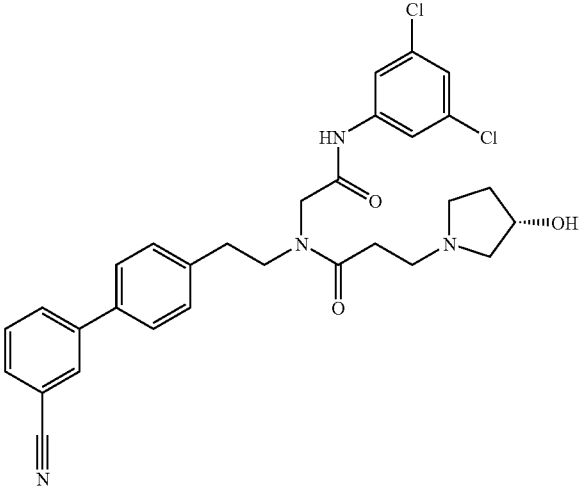 | 565.1617 | 7.2 |
| 7 | 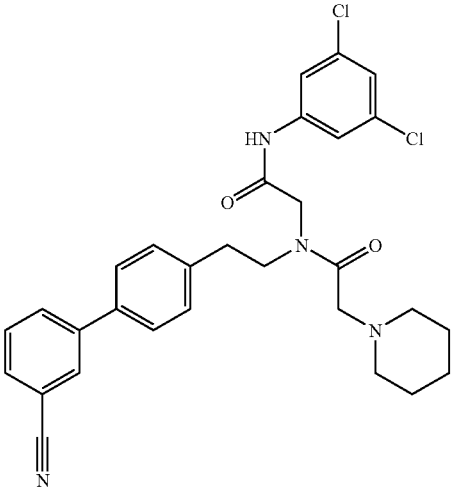 | 549.1830 | 9.3 |
| 8 | 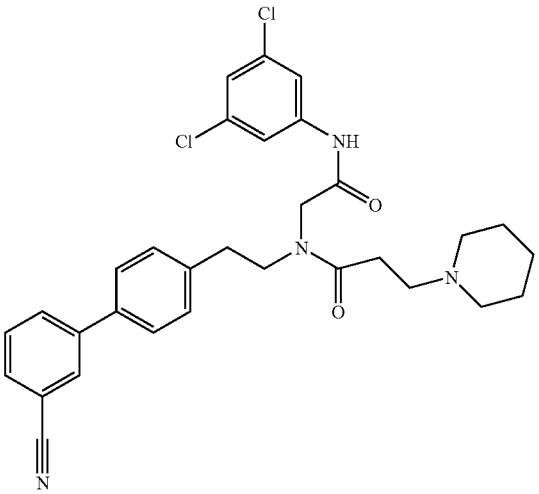 | 549.1835 | 9.5 |

TABLE 1-continued

| Ex. | Structure | HRMS | MCH Ki (nm) |
|---|---|---|---|
| 9 | 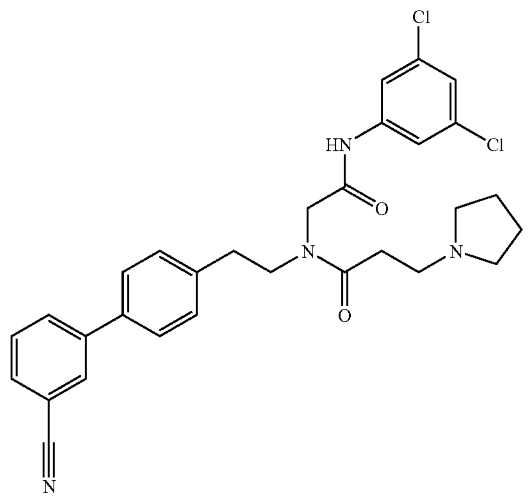 | 549.1835 | 10.0 |
| 10 | 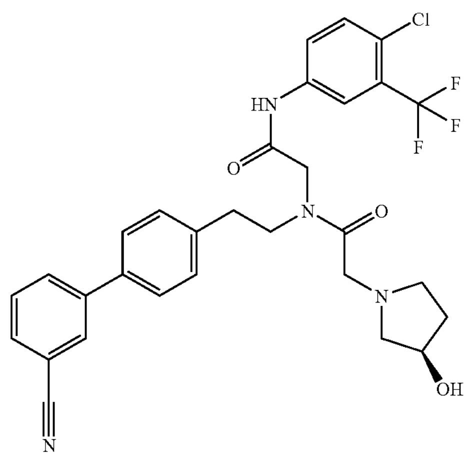 | 585.1872 | 11.0 |
| 11 | 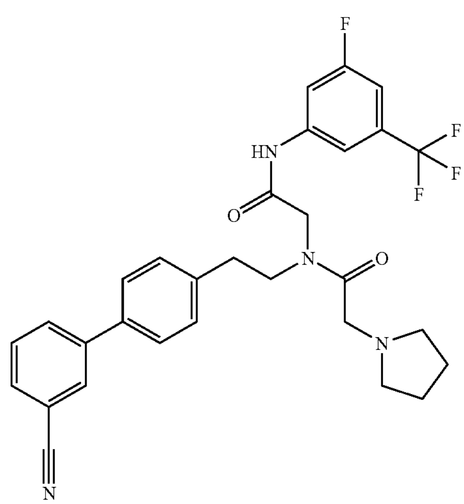 | 553.2236 | 11.7 |

TABLE 1-continued
| Ex. | Structure | HRMS | MCH Ki (nm) |
|---|---|---|---|
| 12 | 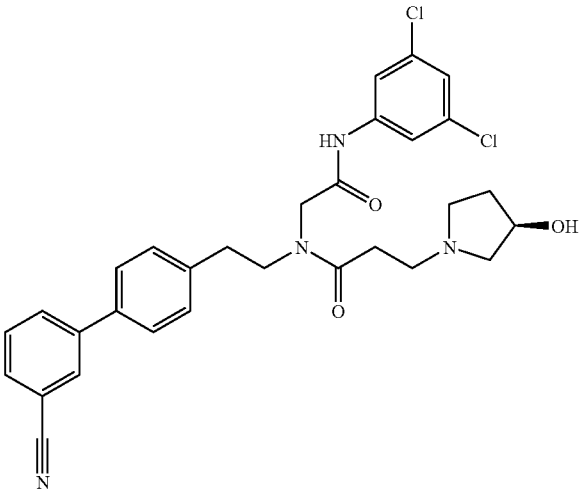 | 565.1782 | 12.0 |
| 13 | 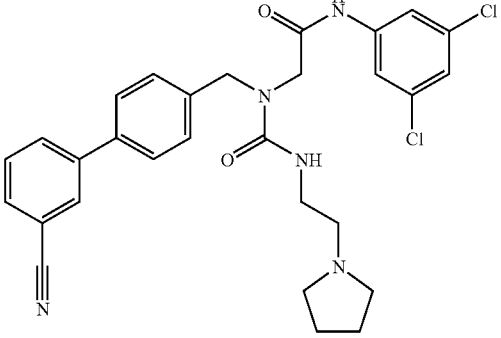 | 550.1768 | 13.0 |
| 14 | 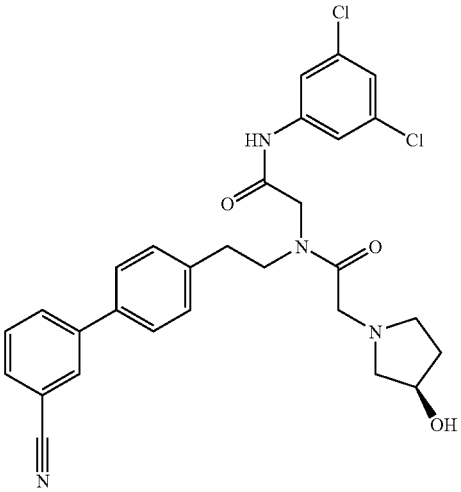 | 551.1607 | 15.0 |

TABLE 1-continued

| Ex. | Structure | HRMS | MCH Ki (nm) |
|---|---|---|---|
| 15 | 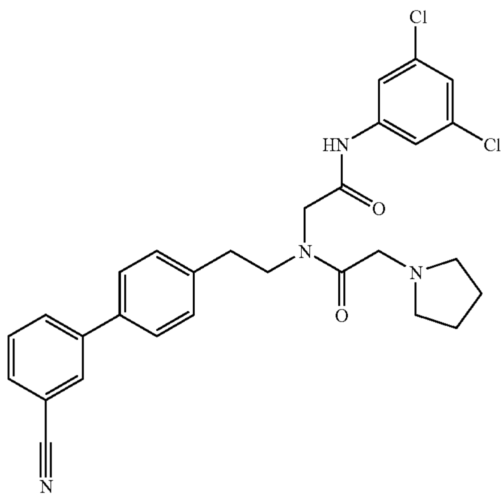 | 535.1658 | 19.0 |
| 16 | 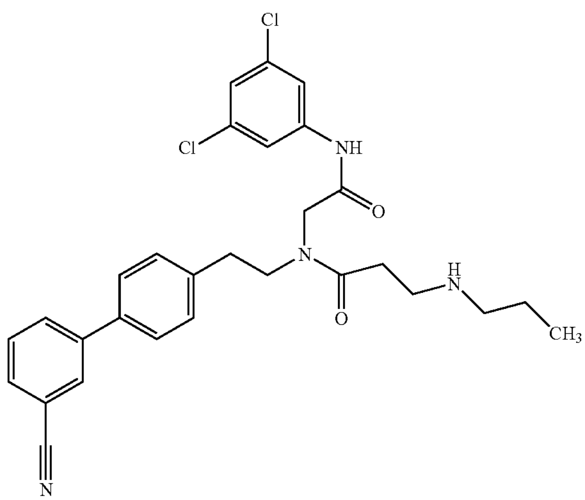 | 537.1816 | 24.0 |
| 17 | 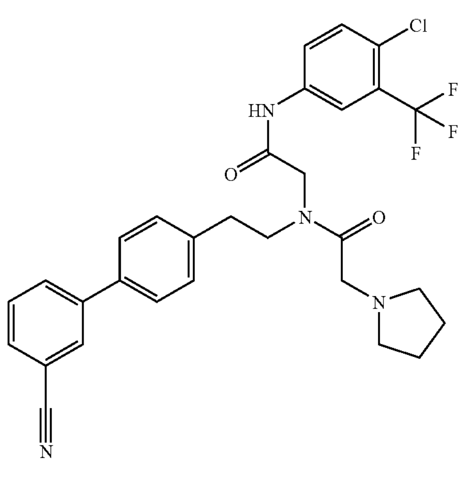 | 569.1936 | 25.0 |

TABLE 1-continued

| Ex. | Structure | HRMS | MCH Ki (nm) |
|-----|-----------|------|-------------|
| 18  | 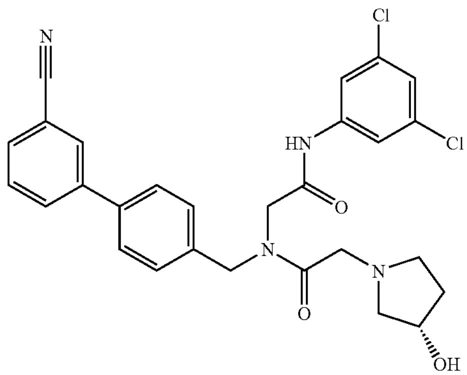          | 537.1454 | 27.0 |
| 19  | 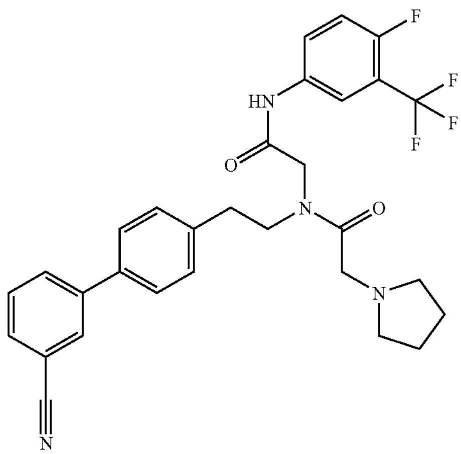          | 553.2230 | 28.0 |
| 20  | 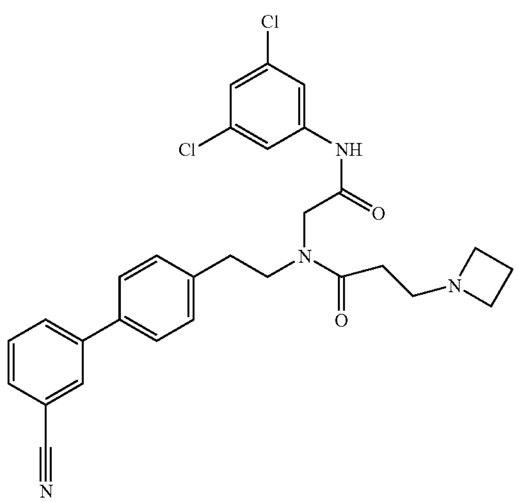          | 535.1662 | 32.0 |

TABLE 1-continued
| Ex. | Structure | HRMS | MCH Ki (nm) |
|---|---|---|---|
| 21 | 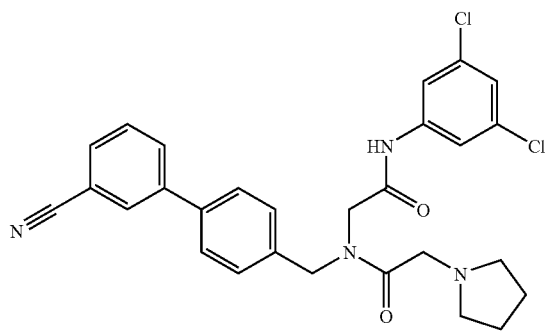 | 521.1500 | 35.0 |
| 22 | 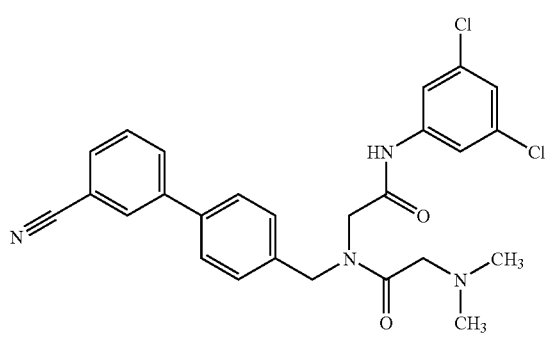 | 495.1348 | 36.0 |
| 23 | 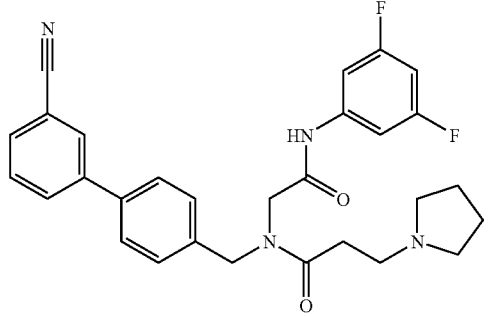 | 549.1835 | 37.0 |
| 24 | 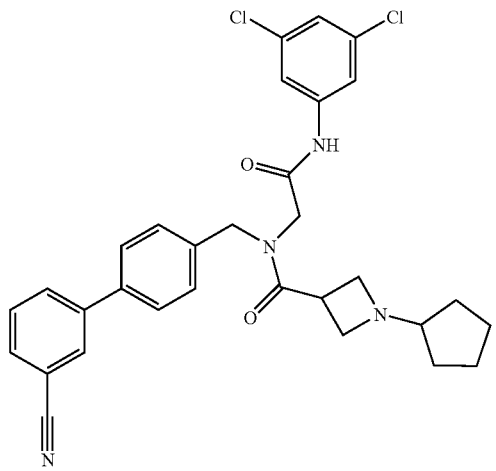 | 561.1830 | 40.0 |

TABLE 1-continued

| Ex. | Structure | HRMS | MCH Ki (nm) |
|---|---|---|---|
| 25 | 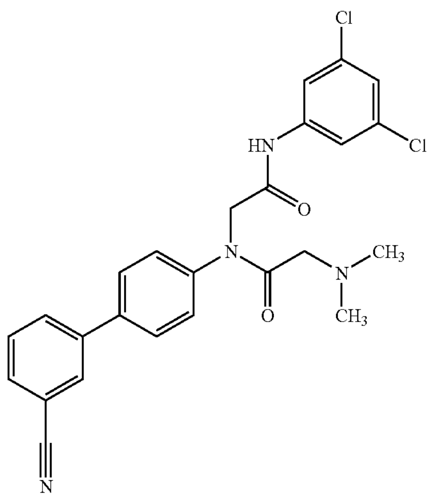 | 481.1198 | 52.0 |
| 26 | 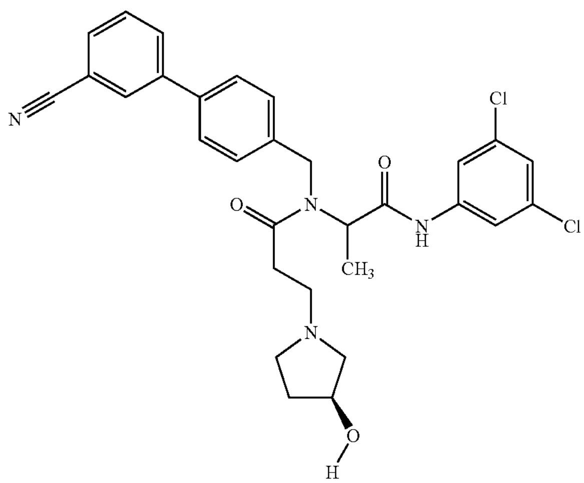 | 565.1783 | 56.0 |
| 27 | 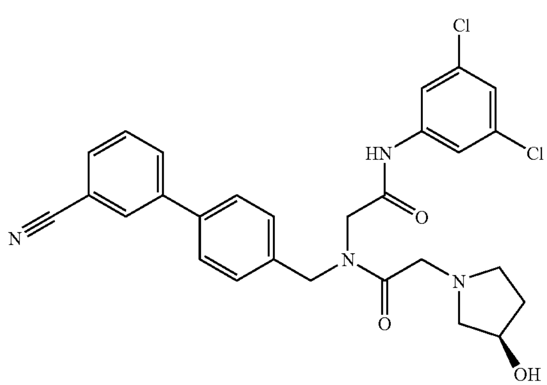 | 537.1452 | 61.0 |

TABLE 1-continued

| Ex. | Structure | HRMS | MCH Ki (nm) |
|---|---|---|---|
| 28 | 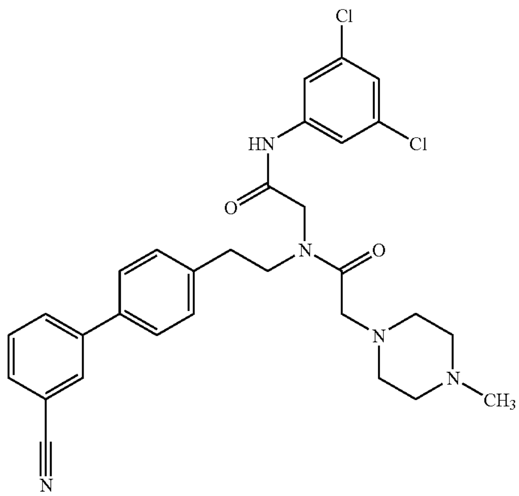 | 564.1933 | 63.0 |
| 29 | 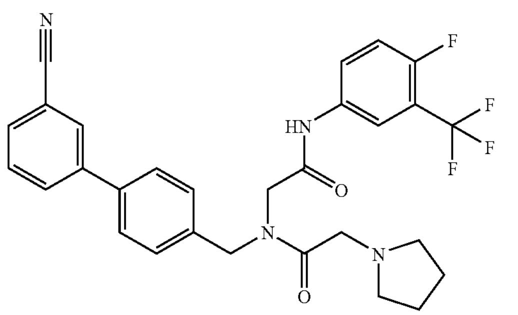 | 539.2065 | 72.0 |
| 30 | 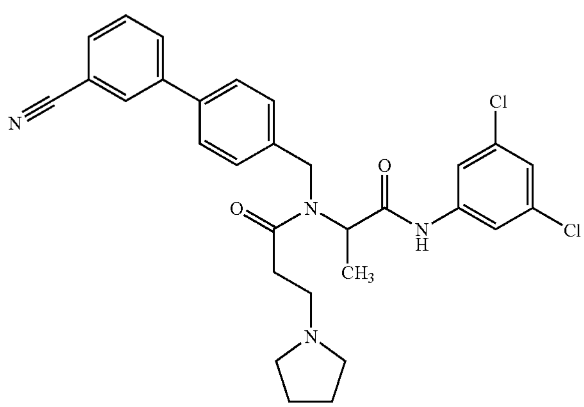 | 549.1817 | 73.0 |

TABLE 1-continued

| Ex. | Structure | HRMS | MCH Ki (nm) |
|---|---|---|---|
| 31 | 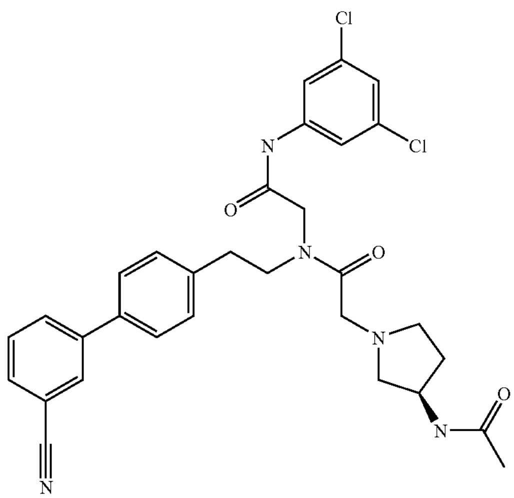 | 592.1875 | 82.0 |
| 32 | 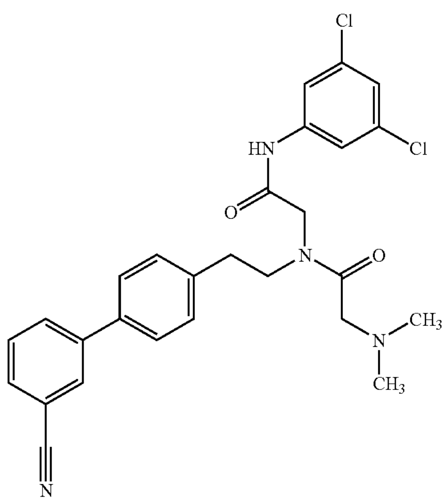 | 509.1504 | 90.0 |
| 33 | 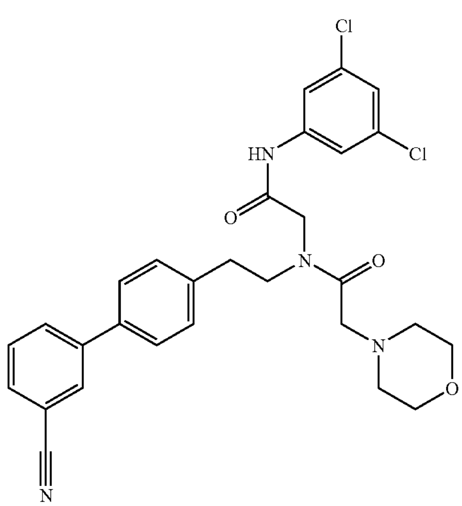 | 551.1612 | |

TABLE 1-continued

| Ex. | Structure | HRMS | MCH Ki (nm) |
|---|---|---|---|
| 34 | 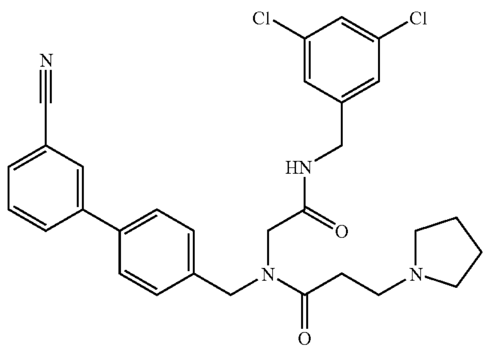 | 503.2259 | |
| 35 | 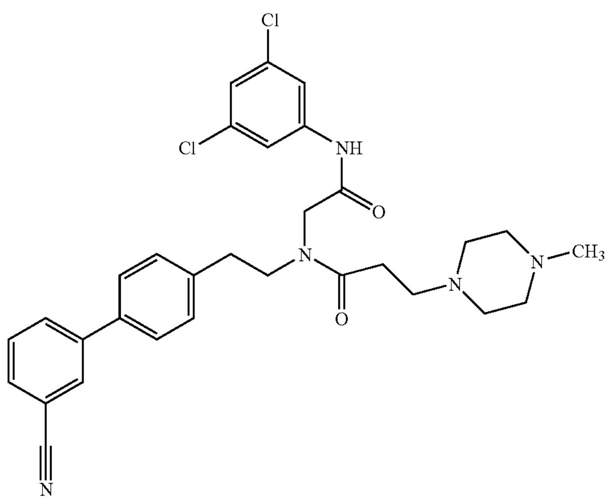 | 578.2080 | |
| 36 | 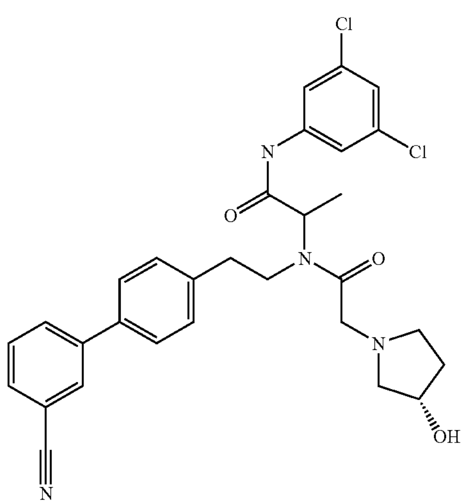 | 565.1777 | 8 |

TABLE 1-continued
| Ex. | Structure | HRMS | MCH Ki (nm) |
|---|---|---|---|
| 37 | 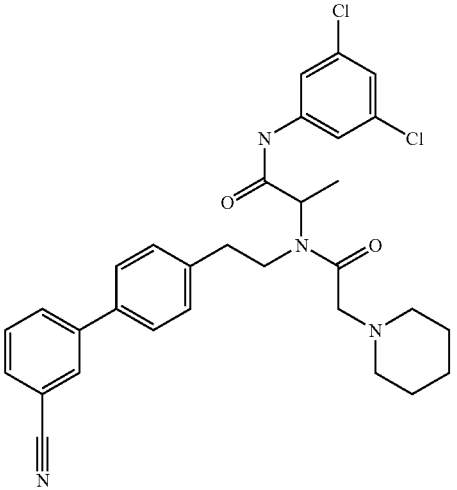 | 563.1975 | 9 |
| 38 | 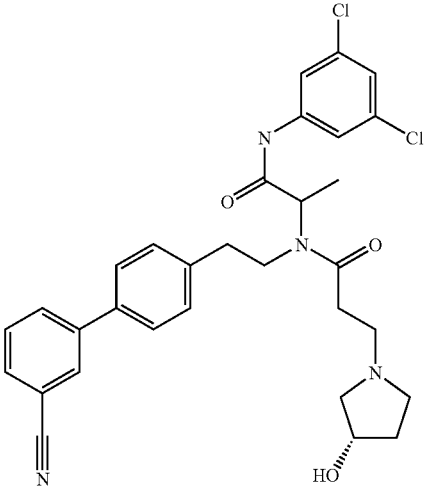 | 579.1921 | |
| 39 | 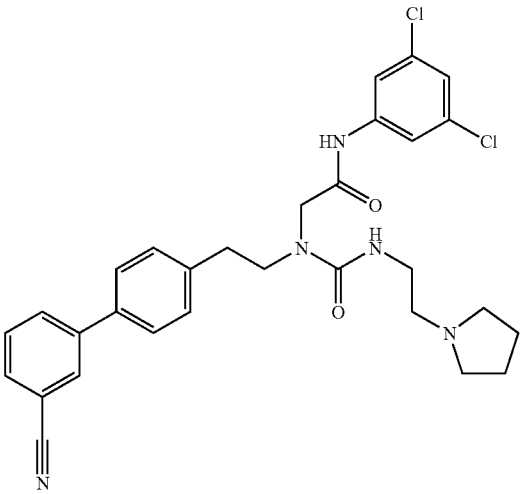 | 564.1940 | |

Examples 40–60 are Prepared According to Scheme 2 and 3

Example 40

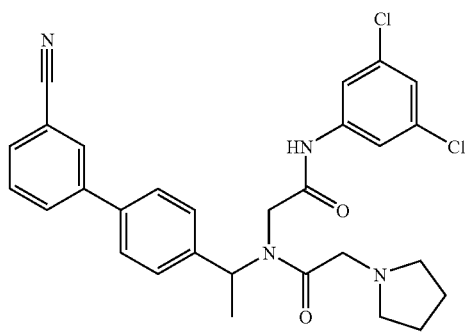

Step 1:

To a stirred solution of 3,5-dichloroaniline (10.4 g, 64.18 mmol) in methylene chloride, cooled to 0° C., was added bromoacetyl bromide (6.71 mL, 77.02 mmol) dropwise. The precipitous mixture stirred at 0° C. for 1 h. The reaction mixture was quenched with 10% NaOH and extracted with methylene chloride. The combined extracts were dried over $Na_2SO_4$ and concentrated to afford 16.21 g (90%) of bromide as a solid.

Step 2:

To a stirred solution of 4-bromo-alpha-methylbenzyl amine (1.0 mL, 6.98 mmol) in 25 mL toluene:ethanol:$H_2O$ (3:1:1) was added 3-cyanophenyl boronic acid (2.05 g, 13.96 mmol), Pd(PPh$_3$)$_4$ (0.81 g, 0.698 mmol) and Na$_2$CO$_3$ (7.39 g, 69.8 mmol). The mixture was degassed with N$_2$, then heated to 100° C. for 24 h. The reaction mixture was concentrated then diluted with EtOAc, washed with H$_2$O, dried over MgSO$_4$, filtered, concentrated and chromatographed over silica gel (eluting with EtOH/EtOAc) to yield 1.14 g (73%) of biaryl amine as an oil.

Step 3:

To a stirred solution of amine formed in step 2, (0.51 g, 2.28 mmol) and bromide formed in step 1, (0.32 g, 1.14 mmol) in CH$_3$CN (8 mL) was added K$_2$CO3 (0.47 g, 3.42 mmol) and heated to 50° C. for 6 h. The reaction mixture was concentrated then diluted with EtOAc, washed with H$_2$O, dried over Na$_2$SO$_4$, concentrated and chromatographed over silica gel (eluting with EtOAc/hexanes) to yield 0.34 g (35%) of an amine.

Step 4:

To a stirred solution of amine formed in step 3, (0.20 g, 0.48 mmol) in methylene chloride (3 mL) was added chloroaceticacid (0.09 g, 0.97 mmol) and EDCl (0.18 g, 0.97 mmol) and stirred at rt for 24 h. The reaction mixture was concentrated and used as a crude mixture for step 5.

Step 5:

To a stirred solution of chloride formed in step 4, (0.48 mmol) in CH$_3$CN (3 mL) was added pyrrolidine (0.2 mL, 2.41 mmol), K$_2$CO$_3$ (0.33 g, 2.41 mmol) and NaI (0.14 g, 0.96 mmol) and heated to 80° C. for 24 h. The reaction mixture was diluted with EtOAc, washed with NaHCO$_3$ solution, dried over MgSO$_4$, filtered and chromatographed (eluting with EtOH/EtOAc) to yield 0.12 g (47%) amine as a solid.

300 MHz—$^1$H NMR (CDCl$_3$)—*9.23, 7.18 (s, 1H); 7.82–7.77 (m, 2H); 7.67–7.44 (m, 6H); 7.40–7.37 (d, 2H); 7.01 (s, 1H); *6.11–6.08, 5.66–5.64 (m, 1H); *4.08, 3.70 (s, 2H); 3.59, *3.47 (s, 2H); *2.90–2.88, 2.69–2.67 (m, 4H); 1.89–1.58 (m, 4H), 1.27–1.21 (t, 3H). Data provided is for a mixture of rotamers, * indicates the minor split peak. HRMS (M+H$^+$) 535.1658 MCH Ki=21 nm Examples 41–60

Employing preparative procedures similar to those described in Example 39, the following compounds were prepared:

TABLE 2

| Ex. | Structure | HRMS | Ki (MCH) |
|---|---|---|---|
| 41 | (structure shown) | 565.1782 | 12.0 |

TABLE 2-continued

| Ex. | Structure | HRMS | Ki (MCH) |
|---|---|---|---|
| 42 | 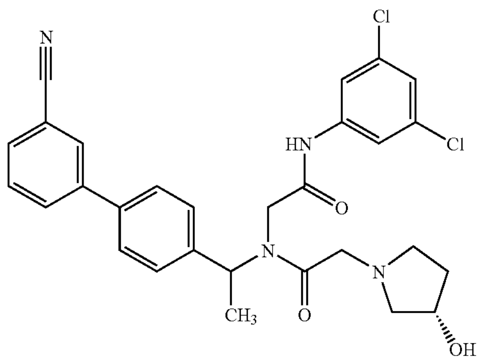 | 551.1607 | 16.0 |
| 43 | 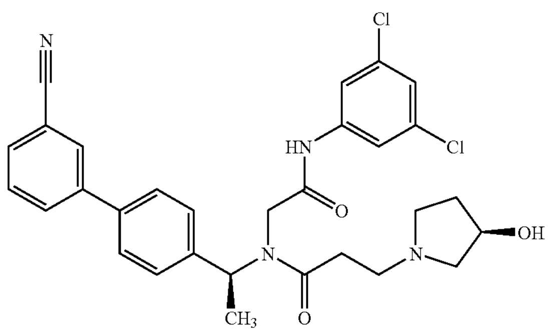 | 565.1783 | 18.0 |
| 44 | 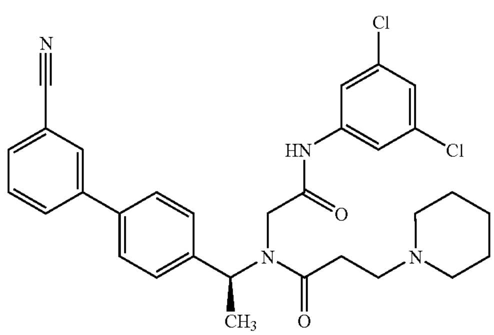 | 563.1986 | 18.0 |
| 45 | 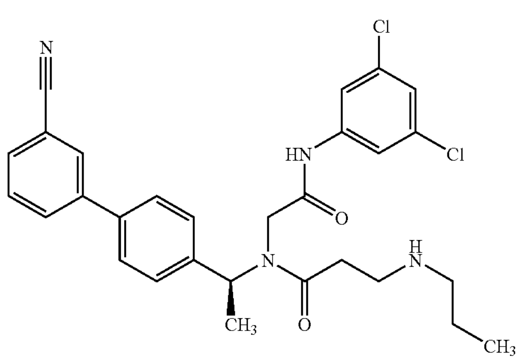 | 537.1824 | 22.0 |

TABLE 2-continued

| Ex. | Structure | HRMS | Ki (MCH) |
|---|---|---|---|
| 46 | 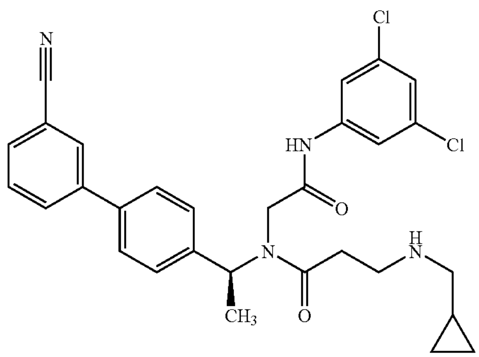 | 549.1819 | 22.0 |
| 47 | 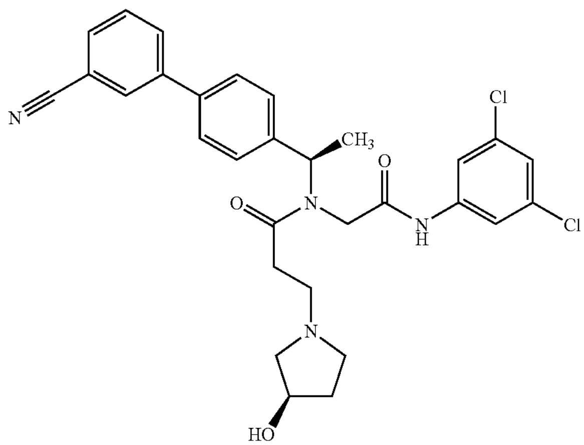 | 565.1773 | 23.0 |
| 48 | 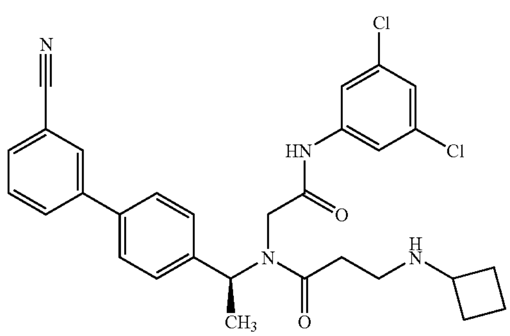 | 549.1825 | 28.0 |
| 49 | 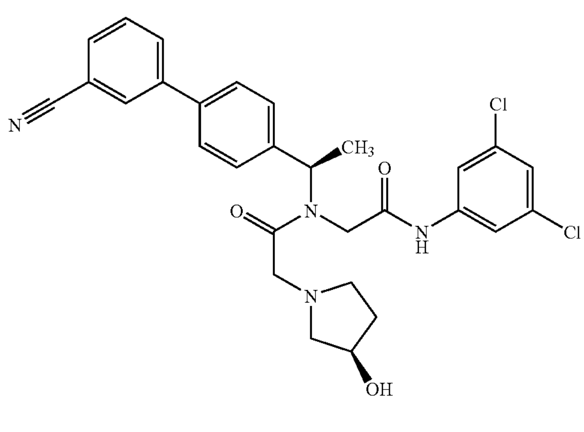 | 551.1617 | 31.0 |

TABLE 2-continued

| Ex. | Structure | HRMS | Ki (MCH) |
|---|---|---|---|
| 50 | 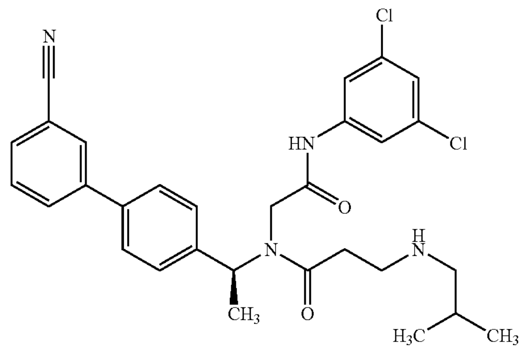 | 551.1987 | 34.0 |
| 51 | 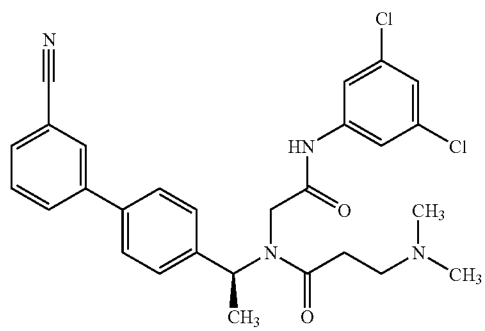 | 523.1658 | 45.0 |
| 52 | 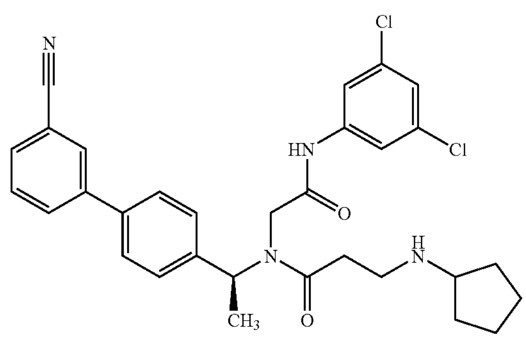 | 563.1986 | 67.0 |
| 53 | 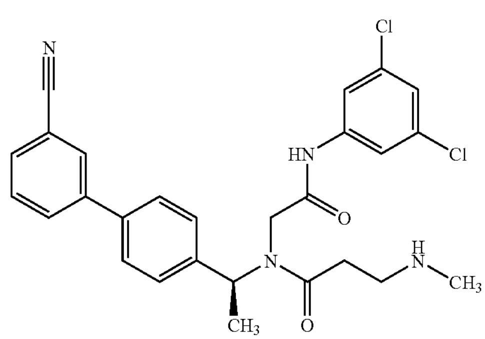 | 509.1519 | 78.0 |

TABLE 2-continued

| Ex. | Structure | HRMS | Ki (MCH) |
|---|---|---|---|
| 54 | 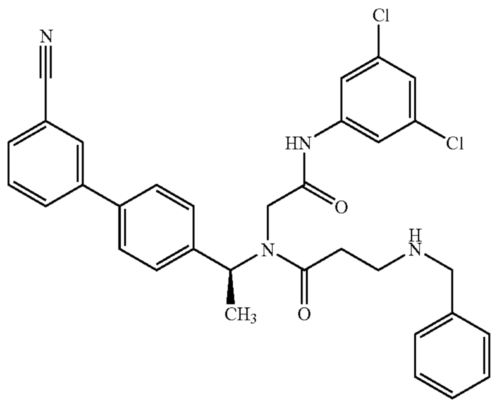 | 585.1858 | |
| 55 | 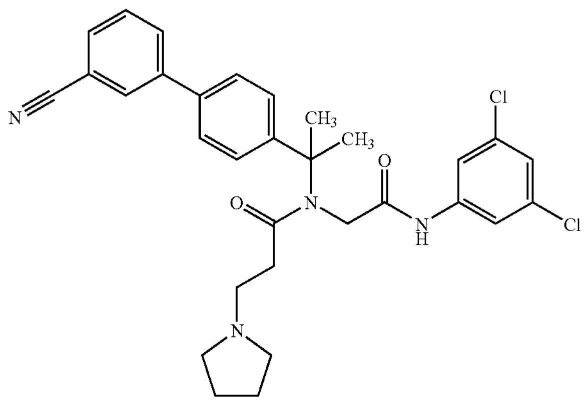 | 563.1981 | |
| 56 | 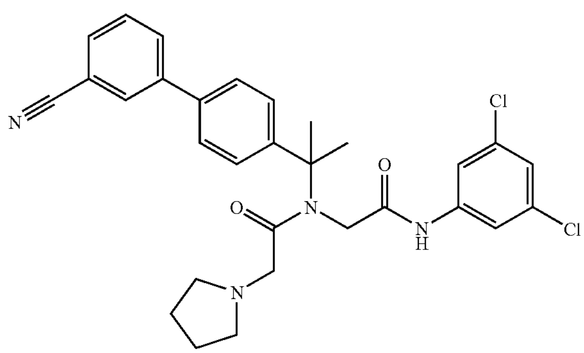 | 549.1835 | |

TABLE 2-continued
| Ex. | Structure | HRMS | Ki (MCH) |
|---|---|---|---|
| 57 | 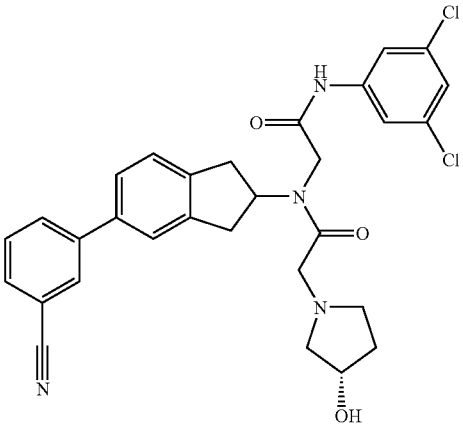 | 563.1621 | |
| 58 | 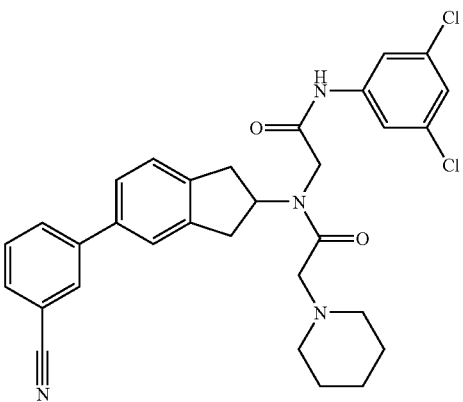 | 561.1829 | |
| 59 | 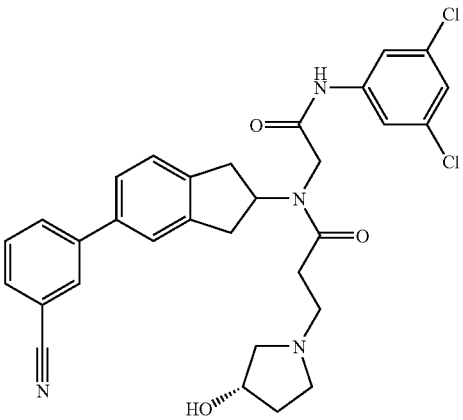 | 577.1777 | |

TABLE 2-continued

| Ex. | Structure | HRMS | Ki (MCH) |
|---|---|---|---|
| 60 | 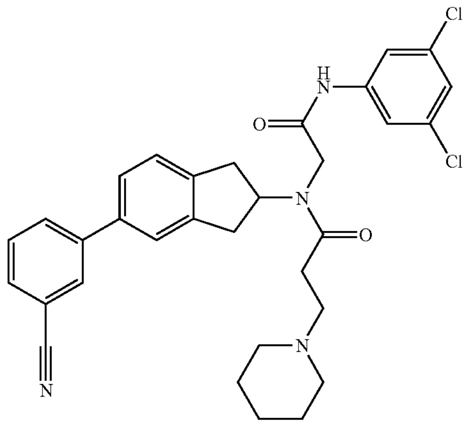 | 575.1989 | |

Examples 61–65 were Prepared According to Scheme 5

Example 61

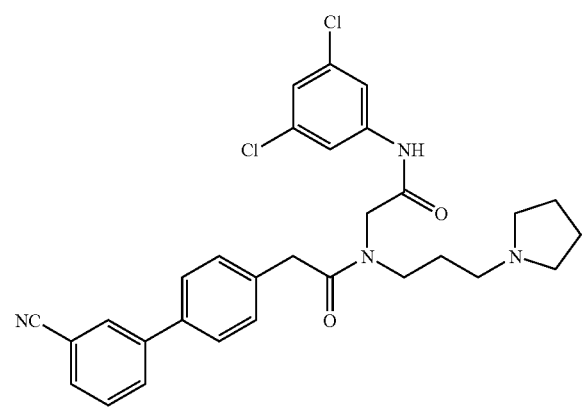

Step 1:

A solution of 3,5-dichloroaniline (1.5 g, 9.26 mmol) in $CH_2Cl_2$ (100 mL) at 0° C. was treated with bromoacetyl bromide (1.05 mL, 12.0 mmol). After 45 min, the reaction mixture was washed with 1N NaOH, $H_2O$, dried and concentrated in vacuo to provide crudebromide (2.66 g) as a white solid.

Step 2:

A solution of crude bromide (300 mg, 1.06 mmol) in $CH_3CN$ (10 mL) was treated with 1-(3-aminopropyl)pyrrolidine (280 □L, 2.20 mmol) and heated to 60° C. After 7 h, the reaction mixture was cooled to ambient temperature, diluted with saturated aqueous $NH_4Cl$ and extracted with EtOAc (3×). The combined organic extracts were washed with saturated aqueous $NaHCO_3$, brine, dried and concentrated in vacuo. The crude product was dissolved in dichloroethane (6 mL) and treated with 4-iodophenylacetic acid (160 mg, 0.610 mmol) followed by diisopropylethyl amine (348 □L, 2.00 mmol). EDCl (156 mg, 0.790 mmol) and HOBT (107 mg, 0.790 mmol) were added and the reaction mixture was heated to 60° C. After 5 h, the reaction mixture was cooled to ambient temperature, diluted with saturated aqueous $NaHCO_3$, and extracted with $CH_2Cl_2$ (3×). The combined organic extracts were dried and concentrated in vacuo. Flash chromatography (2% $MeOH/CH_2Cl_2 \rightarrow 95:4.5:0.5$ $CH_2Cl_2$, MeOH, $NH_4OH$ gradient) afforded Xthe iodoaryl amide (220 mg, 63% over 2 steps) as a yellow oil.

Step 3:

A solution of aryl iodide (100 mg, 0.174 mmol) in $DME/H_2O$ (2:1, 3 mL) was treated with sodium carbonate (28 mg, 0.261 mmol) followed by 3-cyanophenylboronic acid (38 mg, 0.261 mmol). $Pd(dppf)Cl_2$ (16 mg, 0.020 mmol) was added and the reaction mixture was heated to 80° C. After 4 h, the reaction mixture was cooled to ambient temperature, diluted with saturated aqueous $NaHCO_3$, and extracted with EtOAc (2×). The combined organic extracts were dried and concentrated in vacuo. Preparative thin layer chromatography (10% $MeOH/CH_2Cl_2$) furnished the biaryl amide (32.4 mg, 34%) as a clear oil: $^1H$ NMR (300 MHz, $CDCl_3$) □9.16 (s, 1 H), 7.84 (s, 1 H), 7.78 (d, J=7.8 Hz, 1 H), 7.62 (d, J=7.5 Hz, 1 H), 7.56–7.50 (m, 3 H), 7.39–7.35 (m, 4 H), 7.02 (s, 1 H), 4.12 (s, 2 H), 3.97 (s, 2 H), 3.58 (t, J=6.0 Hz, 2 H), 2.48–2.43 (m, 6 H), 1.85–1.78 (m, 6 H). LCMS: 549.1, rt.=5.01 min (M+1), HRMS m/z549.1831 [(M+H)$^+$].

MCH Ki=62 nM

Examples 62–65

Employing preparative procedures similar to those described in Example 61, the following compounds were prepared:

TABLE 3

| Ex. | Structure | HRMS | Ki (MCH) |
|-----|-----------|------|----------|
| 62 | 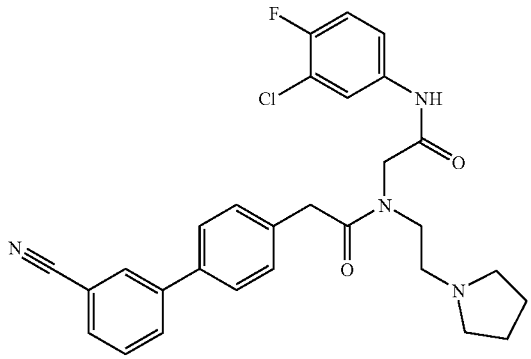 | 519.1967 | |
| 63 | 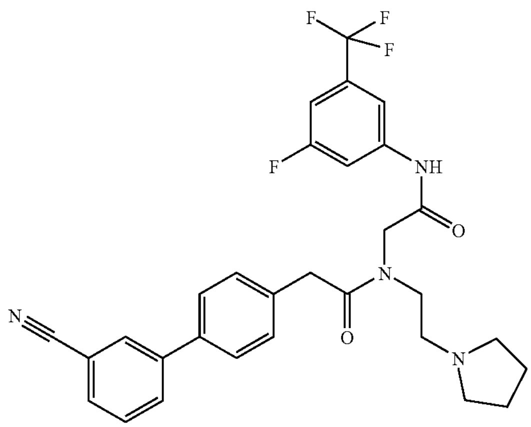 | 553.2236 | |
| 64 | 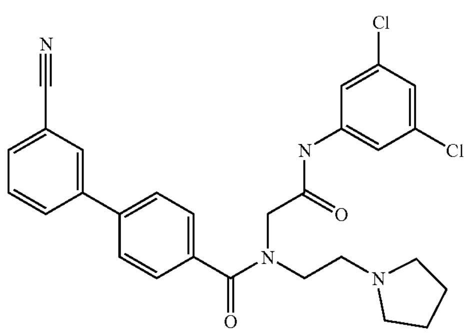 | 521.1515 | |
| 65 | 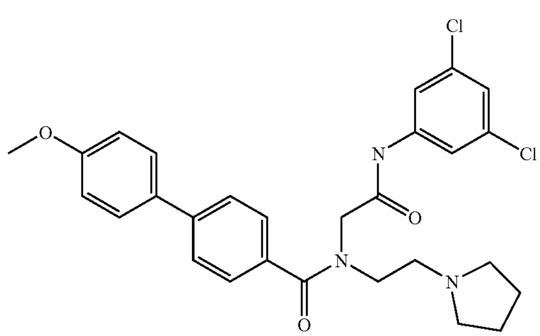 | 526.1669 | |

MCH Receptor Binding Assay:

Membranes from CHO cells expressing the MCH receptor were prepared by lysing cells with 5 mM HEPES for 15 min at 4C. Cell lysates were centrifuged (12.5000×g, 15 min) and the pellet was re-suspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM MGCl$_2$, 10 mM NaCl, 5 mM MnCl$_2$, 0.1% BSA). The membrane/bead mixture was centrifuged (1500×g, 3.5 min), the supernatant was aspirated, and the pellet was re-suspended in 10 ml binding buffer. The centrifugation, aspiration and re-suspension were then repeated. The membrane/bead mixture (100 µl) was then added to 96-well plates containing 50 µl of 500 pM [$^{125}$I]-MCH (NEN) and 50 ml of the appropriate concentration of compound (4× the desired final concentration). Nonspecific binding was determined by including 1 µM MCH in the binding reaction. The binding reaction was incubated at room temperature for 2 h. Plates were then analyzed in a TOPCOUNT microplate scintillation counter (Packard). Data was analyzed and Ki values were determined using GraphPad Prim.

For the compounds of this invention, a range of MCH receptor binding activity (Ki values) of from about 3 nM to about 1500 nM was observed. Compounds of this invention have a binding activity in the range of from about 3 nM to about 1000 nM.

While the present invention has been described in conjunction with the specific embodiments set forth above, many alternatives, modifications and other variations thereof will be apparent to those of ordinary skill in the art. All such alternatives, modifications and variations are intended to fall with the spirit and scope of the present invention.

What is claimed:

1. A compound of formula I:

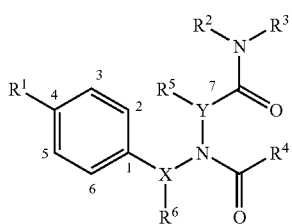

formula I or a pharmaceutically acceptable salt or solvate of said compound, wherein:

X is a single bond, —C—, —CH— or alkylene, and when X is a single bond, R$^6$ is absent and the carbon atom marked 1 is directly attached to N of N—Y;

Y is a single bond, —C—, —CH— or alkylene, and when Y is a single bond, R$^5$ is absent and the carbon atom marked 7 is directly attached to N of N—X;

R$^1$ is aryl or heteroaryl, wherein each of said aryl or heteroaryl can be unsubstituted or optionally independently substituted with one or more moieties which can be the same or different, each moiety being independently selected from the group consisting of CN, CF$_3$, halogen, alkyl, cycloalkyl, cycloalkylalkyl, haloalkyl, haloalkoxy, alkoxy and OH;

R$^2$ is H, alkyl, aryl or aralkyl wherein each of said aryl or aralkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH;

R$^3$ is H, alkyl, aryl or aralkyl wherein each of said aryl or aralkyl can be unsubstituted or optionally independently substituted with one or more moieties which can be the same or different, each moiety being independently selected from the group consisting of CF$_3$, halogen, alkyl, cycloalkyl, cycloalkylalkyl, haloalkyl, haloalkoxy, alkoxy and OH;

R$^4$ is selected from the group consisting of

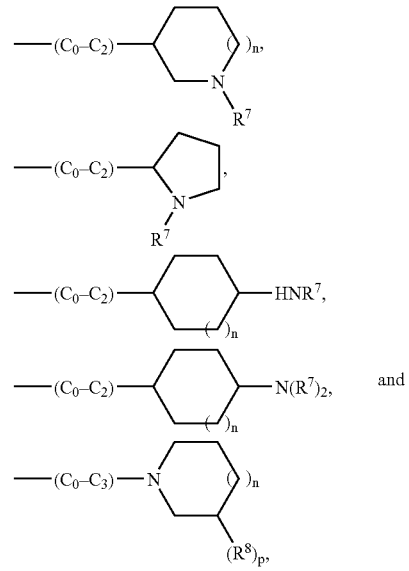

wherein each R$^7$ in said —N(R$^7$)$_2$, can be the same or different and each R$^7$ is H, alkyl, cycloalkyl or aryl, wherein each of said alkyl, aryl or cycloalkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH; or each R$^7$ can be joined together and with the nitrogen to which they are attached to form a 3 to 7-membered heterocyclyl ring;

n is 0;

p is 0 to 5 and when p is >1, the number of p moieties can be the same or different;

R$^5$ is H or 1 or 2 substituents independently selected from alkyl or cycloalkyl;

R$^6$ is H or 1 or 2 substituents independently selected from alkyl or cycloalkyl; and R$^8$ is H, OH, alkoxy, alkyl, cycloalkyl, aryl, —N(H)R$^7$, —N(H)C(O)alkyl, —N(H)C(O)aryl, —N(H)C(O)N(H)alkyl, —N(H)C(O)N(H)aryl, —N(H)S(O$_2$)alkyl or —N(H)S(O$_2$)aryl;

with the proviso that the carbons shown marked 1 and 6 on the aromatic ring, along with X—R$^6$, can optionally form a 4 to 8 membered ring system.

2. The compound of claim 1 of formula Ia:

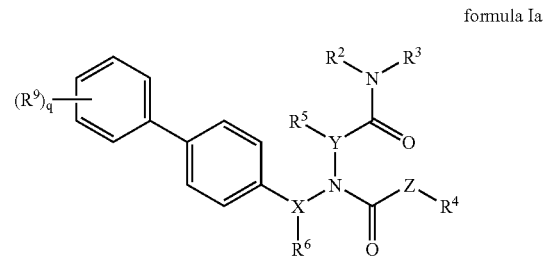

formula Ia or a pharmaceutically acceptable salt or solvate of said compound, wherein:

q is 0 to 5 and when q is >1, the number of q moieties can be the same or different;

X is —CH— or alkylene;

Y is a CH2;

$R^2$ is H, alkyl, aryl or aralkyl wherein each of said aryl or aralkyl can be unsubstituted or optionally independently substituted with one or more moieties which can be the same or different, each moiety being independently selected from the group consisting of halogen, alkyl, cycloalkyl, cycloalkylalkyl, haloalkyl, haloalkoxy, alkoxy and OH;

$R^3$ is H, alkyl, aryl or aralkyl wherein each of said aryl or aralkyl can be unsubstituted or optionally independently substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH; $R^4$ is

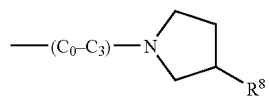

$R^5$ and $R^6$ can be the same or different, and are independently H or alkyl;

$R^8$ is H, OH, alkoxy, alkyl, cycloalkyl, aryl, —N(H)$R^7$, —N(H)C(O)alkyl, —N(H)C(O)N(H)alkyl or —N(H)S(O_2)alkyl; and $R^9$ is alkyl, F, Cl, Br, I, $NO_2$, $C(O)NH_2$, C(O)N(H)R or N(H)C(O)R, wherein R is alkyl, $OCF_3$, $CH_3$ or CN.

3. The compound of claim 2 wherein $R^9$ is a 3 or 4-substituted aryl.

4. The compound of claim 2 wherein $R^9$ is a 3-cyano substituted aryl.

5. The compound of claim 1 of formula Ib:

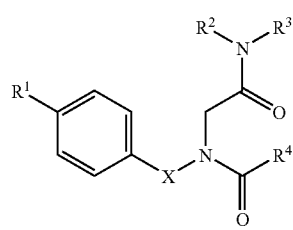

formula Ib or a pharmaceutically acceptable salt or solvate of said compound, wherein:

X is an alkylene group;

$R^1$ is 3-cyanophenyl;

$R^2$ is H;

$R^3$ is a phenyl, wherein said phenyl is substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH; $R^4$ is

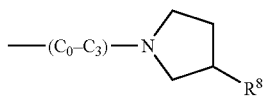

and $R^8$ is H, alkyl, cycloalkyl, aryl, —N(H)alkyl, —N(H)aryl, OH, alkoxy, —N(H)C(O)alkyl, —N(H)C(O)N(H)alkyl or —N(H)S(O_2)alkyl.

6. The compound of claim 1 of formula Ic:

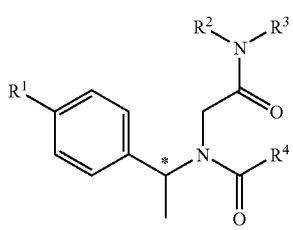

methyl group is (S), (R) or racemic formula Ic or a pharmaceutically acceptable salt or solvate of said compound, wherein:

$R^1$ is 3-cyanophenyl;

$R^2$ is H;

$R^3$ is a phenyl, wherein said phenyl is substituted with one or more moieties which can be the same or different, each moiety being independently selected from the group consisting of $CF_3$, halogen, alkyl, cycloalkyl, cycloalkylalkyl, haloalkyl, haloalkoxy, alkoxy and OH;

$R^4$ is

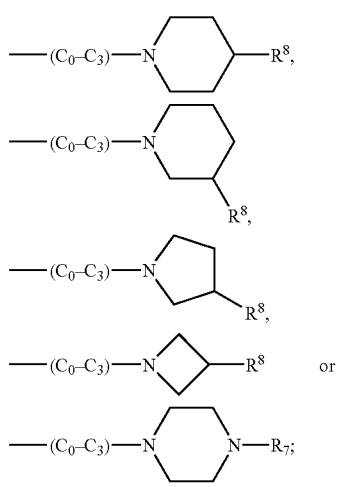

and $R^8$ is H, alkyl, cycloalkyl, aryl, —N(H)alkyl, —N(H)aryl, OH, alkoxy, —N(H)C(O)alkyl, —N(H)C(O)N(H)alkyl or —N(H)S(O_2)alkyl.

7. A compound of claim 1 selected from the group consisting of:

71
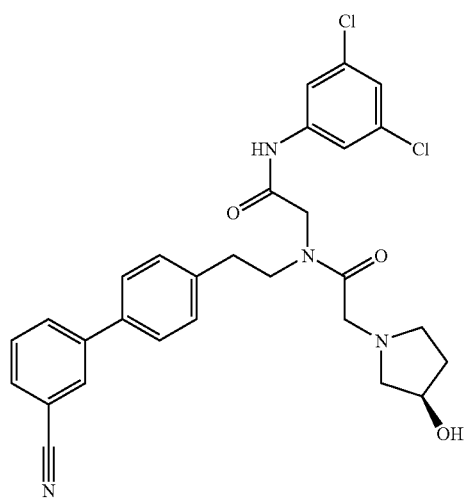
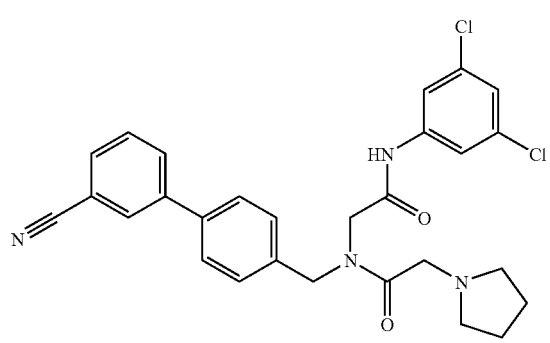
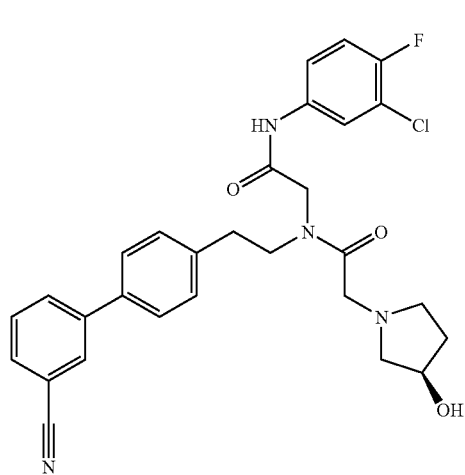
72
-continued
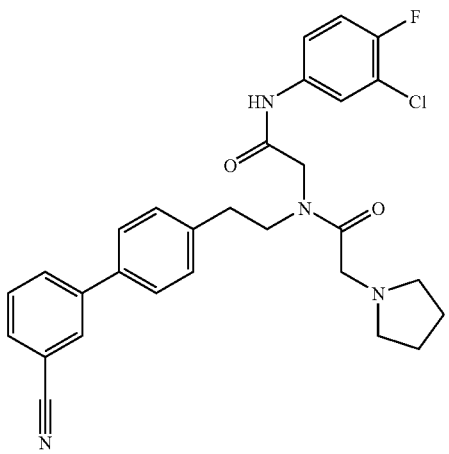
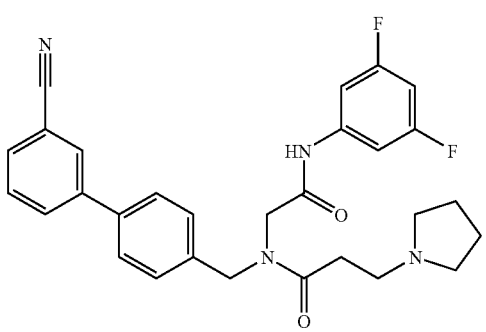
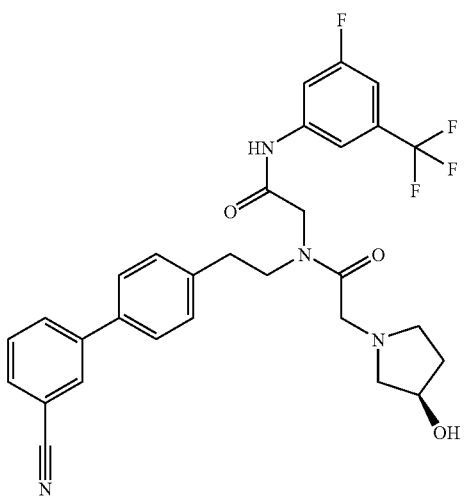

73
-continued
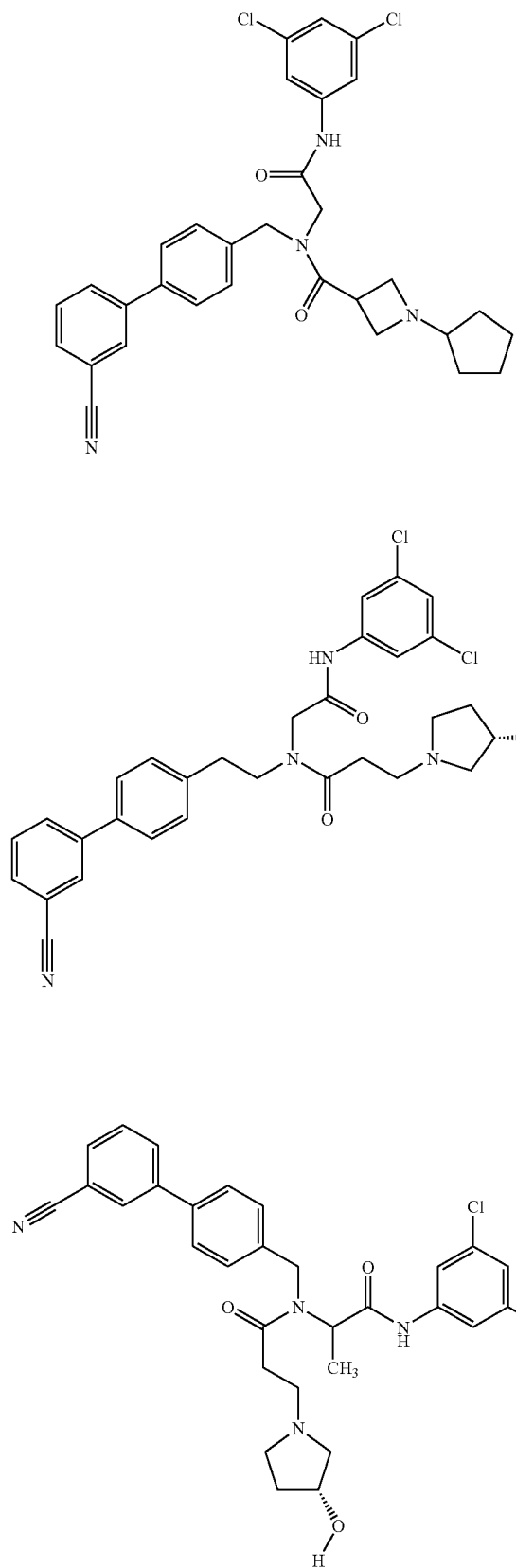
74
-continued
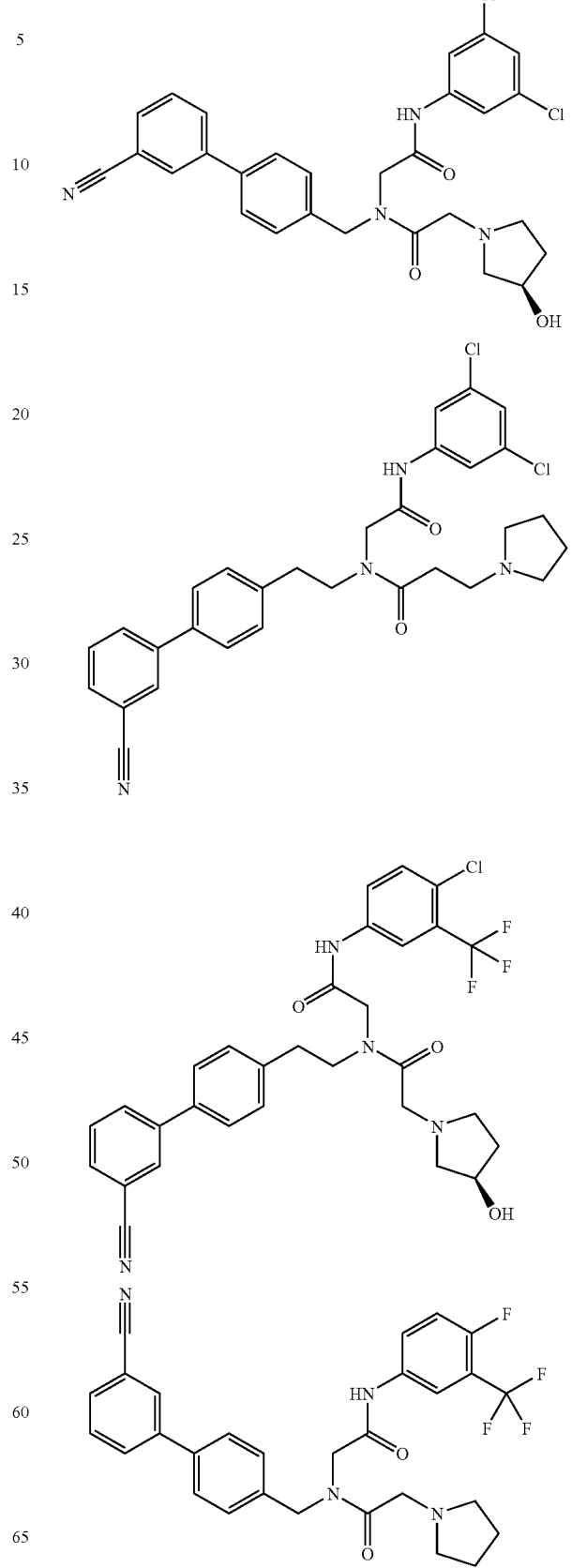

75
-continued
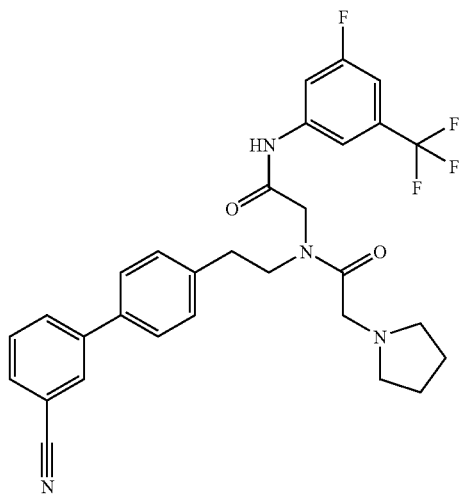
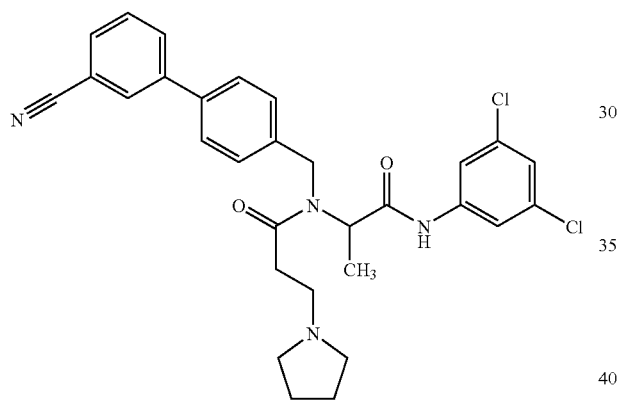
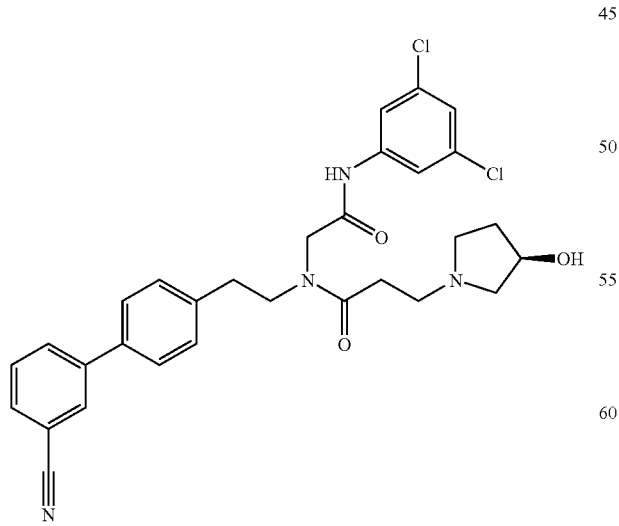
76
-continued
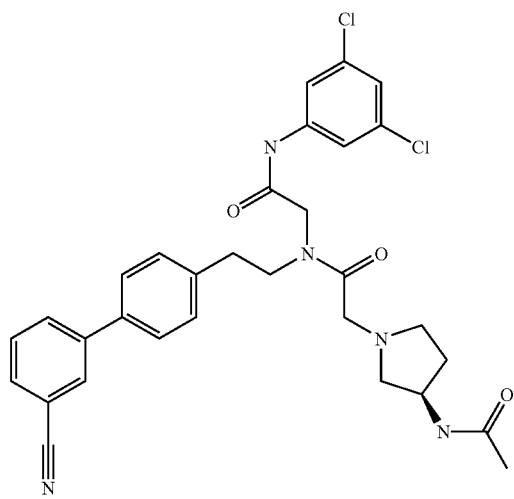
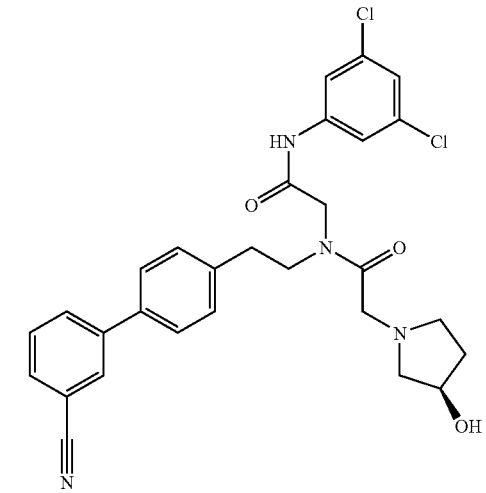

77 78
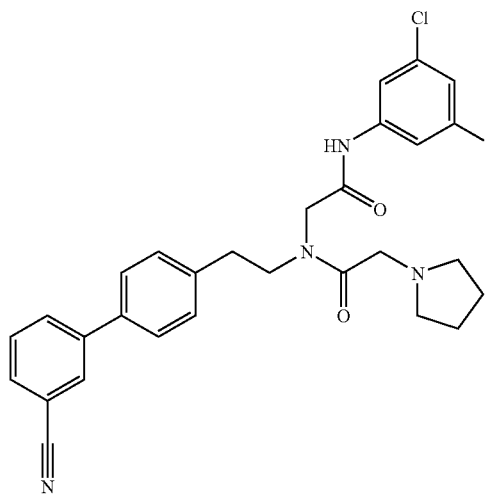
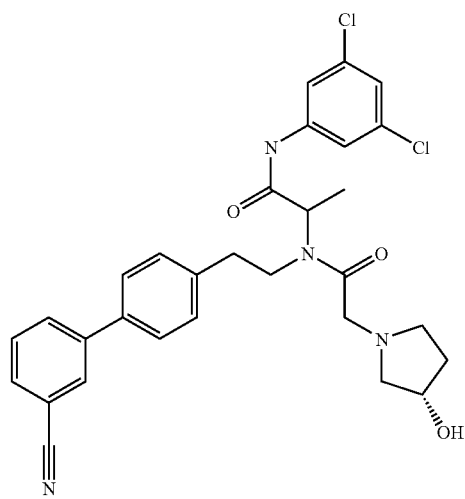
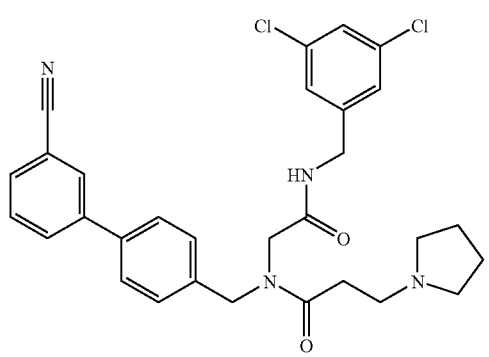
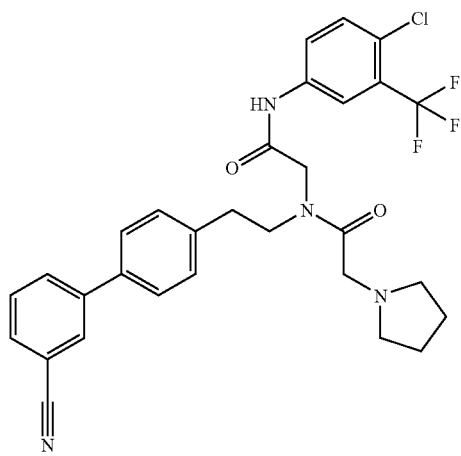

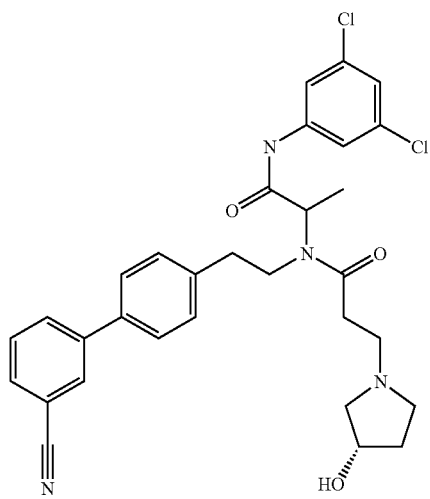
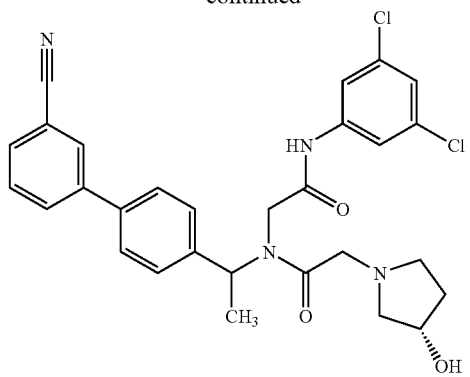
and
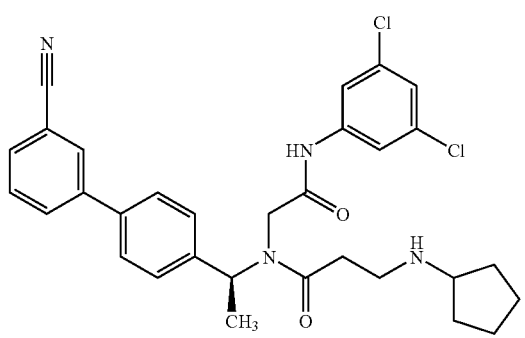
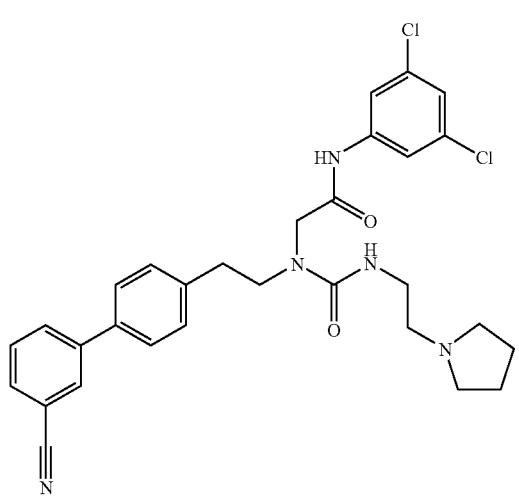
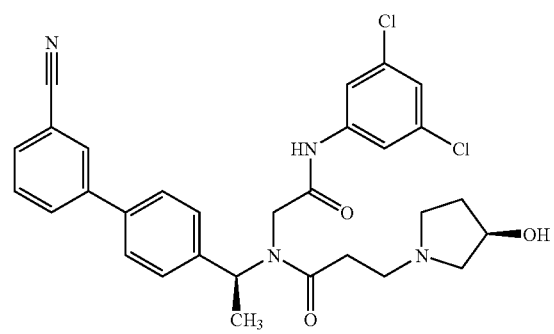
or a pharmaceutically acceptable salt or solvate of said compound.
8. The compound of claim 1 selected from the group consisting of
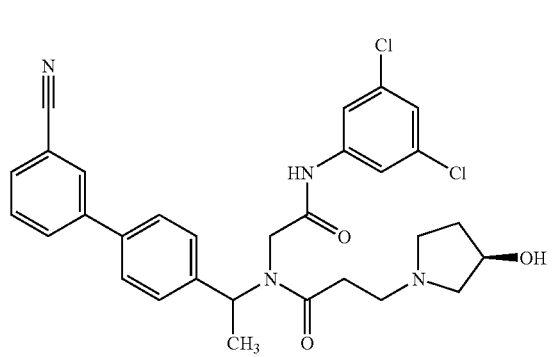
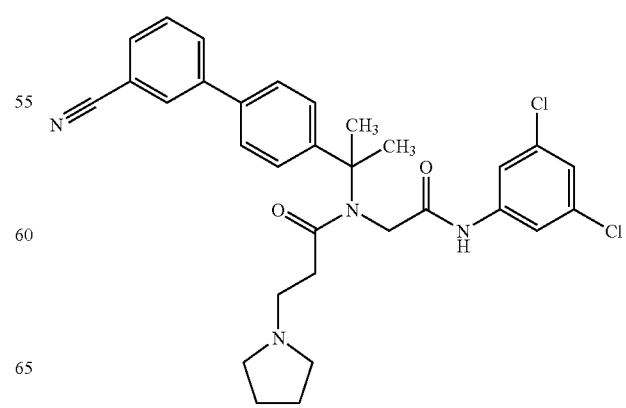

-continued
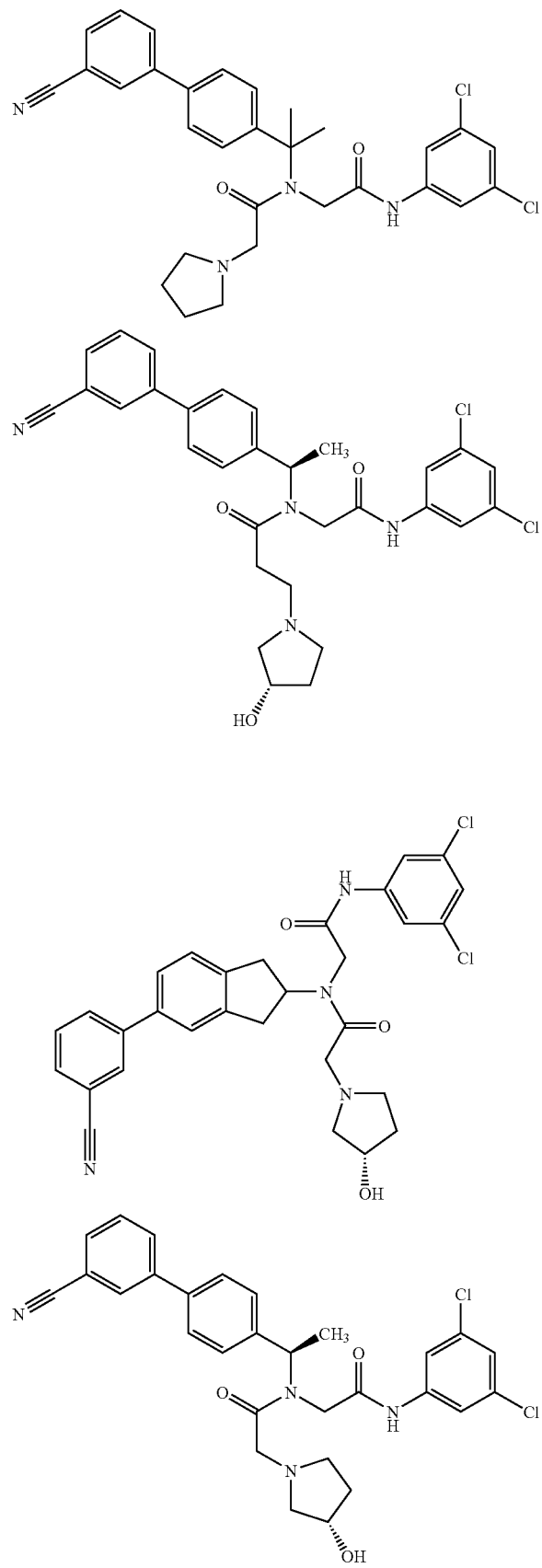
and
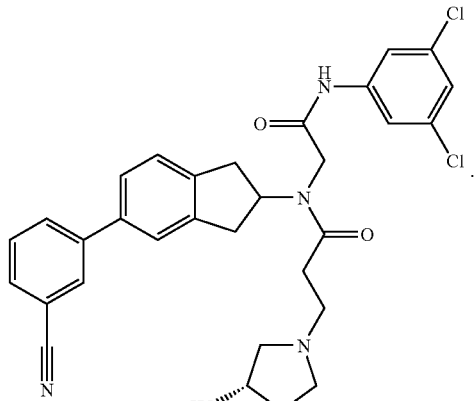
or a pharmaceutically acceptable salt or solvate of said compound.
9. The compound of claim 1 of the formula
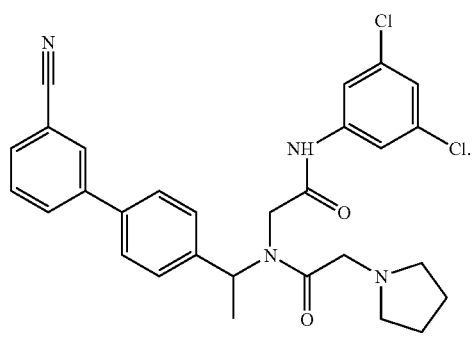
or a pharmaceutically acceptable salt or solvate of said compound.
10. The compound of claim 1 of the formula
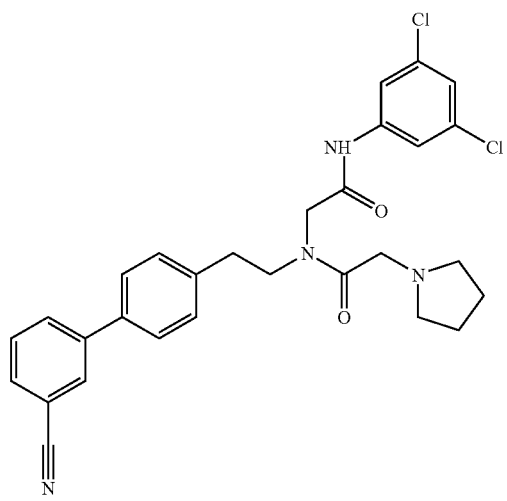
or a pharmaceutically acceptable salt or solvate of said compound.

11. The compound of claim 1 of the formula

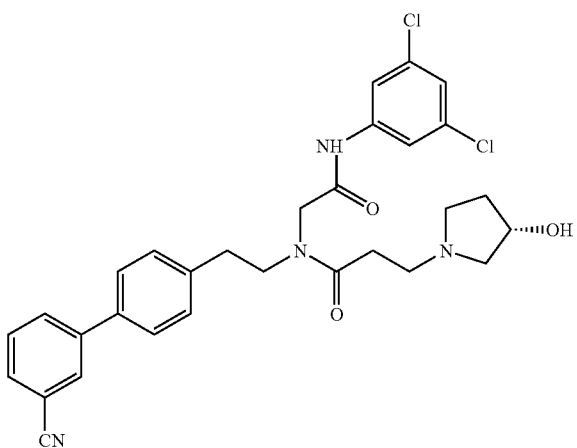

or a pharmaceutically acceptable salt or solvate of said compound.

12. A method of treating a metabolic disorder, eating disorder or diabetes comprising administering an effective amount of a compound of claim 1 to a patient in need of such treatment.

13. The method of claim 12 wherein said eating disorder is hyperphagia.

14. The method of claim 12 wherein said metabolic disorder is obesity.

15. A method of treating disorders associated with obesity comprising administering to a patient in need of such treatment a therapeutically effective amount of a compound of claim 1 or a pharmaceutically acceptable salt of said compound.

16. The method of claim 15 wherein said disorders associated with obesity are type II diabetes, insulin resistance, hyperlipidemia and hypertension.

17. A method of treating an eating disorder which comprises administering to a patient in need of such treatment
an amount of a first compound, said first compound being a compound of claim 1, or a pharmaceutically acceptable salt of said compound;
an amount of at least one more compound, said other compound (b) is selected from an antiobesity and/or anorectic agent such as a $\beta_3$ agonist, a thyromimetic agent, an anoretic agent, and an NPY antagonist;
wherein the amounts of the (a) and (b) compounds result in a therapeutic effect.

18. A pharmaceutical composition which comprises a therapeutically effective amount of a composition comprising:
a first compound, said first compound being a compound of claim 1, or a pharmaceutically acceptable salt of said compound;
an amount of at least one more compound, said other compound (b) is selected from an antiobesity and/or anorectic agent such as a $\beta_3$ agonist, a thyromimetic agent, an anoretic agent, and an NPY antagonist; and
a pharmaceutically acceptable carrier.

19. A pharmaceutical composition which comprises a therapeutically effective amount of a composition comprising:
a first compound, said first compound being a compound of claim 1, or a pharmaceutically acceptable salt of said compound;
at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide; and a pharmaceutically acceptable carrier.

20. A pharmaceutical composition comprising a therapeutically effective amount of at least one compound of claim 1 in combination with at least one pharmaceutically acceptable carrier.

21. A process for making a pharmaceutical composition comprising combining at least one compound of claim 1 and at least one pharmaceutically acceptable carrier.

* * * * *